(12) United States Patent
Soll et al.

(10) Patent No.: US 7,593,952 B2
(45) Date of Patent: Sep. 22, 2009

(54) ENHANCED MEDICAL TREATMENT SYSTEM

(76) Inventors: Andrew H. Soll, 1665 Michael La., Pacific Palisades, CA (US) 90272; Liana Violet Soll, 2621 Centinela Ave., #4, Santa Monica, CA (US) 90405

( * ) Notice: Subject to any disclaimer, the term of this patent is extended or adjusted under 35 U.S.C. 154(b) by 0 days.

(21) Appl. No.: 09/289,044

(22) Filed: Apr. 9, 1999

(65) Prior Publication Data

US 2003/0055679 A1    Mar. 20, 2003

(51) Int. Cl.
*G06F 17/00* (2006.01)
(52) U.S. Cl. .................... 707/102; 707/100; 707/101; 707/104.1
(58) Field of Classification Search ......... 707/100–102; 705/1, 2, 3; 600/300, 301; 434/236
See application file for complete search history.

(56) References Cited

U.S. PATENT DOCUMENTS

| | | | | |
|---|---|---|---|---|
| 6,039,688 A | * | 3/2000 | Douglas et al. | 600/300 |
| 6,149,585 A | * | 11/2000 | Gray | 600/300 |
| 6,177,940 B1 | * | 1/2001 | Bond et al. | 705/3 |
| 6,208,974 B1 | * | 3/2001 | Campbell et al. | 705/3 |
| 6,234,964 B1 | * | 5/2001 | Iliff | 600/300 |
| 6,269,339 B1 | * | 7/2001 | Silver | 705/2 |
| 6,283,761 B1 | * | 9/2001 | Joao | 434/236 |

* cited by examiner

*Primary Examiner*—Sana Al-Hashemi
(74) *Attorney, Agent, or Firm*—Morgan, Lewis & Bockius LLP; Steven D. Underwood, Esq.

(57) ABSTRACT

This invention deals with an enhanced medical treatment system which seeks input from the patient and the physician about the medical problems faced by the patient. It analyzes this information and seeks to guide physicians to a correct diagnosis of the complaint. It also seeks to educate the patient about his/her medical problems and provides information about the problem. It is able to store all this information, so that a continues record of the patient's visits and problems is kept on file and the physician is able to utilize the medical history to solve the patient's current problems. With this system in place the medical establishment will be able to improve health care delivery to the patients and be able to better manage the process of the providing health care. Furthermore, this system will also lower the cost of providing health care without compromising on the quality of health care.

14 Claims, 27 Drawing Sheets

ENHANCED MEDICAL TREATMENT SYSTEM

FIELD OF THE INVENTION

The present invention relates to systems for disease management, and more specifically to a practical computer system and clinical management methodology that enhances the quality and cost-effectiveness of health care in real practice settings. The approach is to integrate a plurality of separate functions into a seamless diagnostic and treatment system that enhances patient assessment, activates (primes) and educates patients to become maximally involved in their care, and improves the efficiency of physician management process (Table 1). The system will simultaneously enhance health care delivery and capture data regarding the process and outcomes of care, thereby allowing the quality and efficiency of specific treatments or of an overall management process to be measured and improved.

TABLE 1

Goals and Functions of the Invention

1. Directly collect, analyze, and verify comprehensive, accurate patient data to facilitate and improve patient evaluation
2. Use a patient-friendly, intuitive interface that allows:
   direct patient input of data
   simplification of computer use (e.g. touch screens)
   use of screening questions that branch to detailed questions only where relevant to patient's complaints
   individualized strategy for computerized patient interaction (adapts to patient characteristics, e.g., age, gender, language, education level)
3. Create a computer system that facilitates patient-centered care at multiple levels:
   facilitate communication between patients and physicians
   guide and educate patients on symptoms and health issues
   "activate" (prime) patients to provide a more accurate, comprehensive history and to be more involved in their care
   collect and present the patient's health questions and concerns to physicians
   collect and present comprehensive biopsychosocial data to physicians
   assess patient response to and satisfaction with care
4. Improve the efficiency and effectiveness of physician process:
   provide a physician-friendly, easy-to-use computer system
   present patient data in a problem-oriented format for efficient review and editing
   expedite generation of the clinical report for the record
   facilitate generation of orders for tests, medications, procedures or referrals
   in follow-up mode, improve physician access to prior patient records using a concise, problem-oriented format
5. Improve the outcomes and cost-effectiveness of care
6. Build comprehensive process and outcome database to:
   capture the clinical presentation of common disorders, thereby improving diagnostic accuracy and efficiency
   assess the value of various therapeutic interventions
   assess the value of various elements of patient-centered care (see 3 above)
   support rigorous clinical investigation in real practice settings to measure and improve the outcomes of care

BACKGROUND OF THE INVENTION

Implementing Health Care Advances in Practice Settings. Recent technological advances have engulfed the health care field, but have not generally resulted in improved health care for many common conditions. The sophistication of diagnostic tools has increased ten-fold in the last two decades, including such exotic technologies as nuclear magnetic resonance imaging to detect the spin state of individual protons within a patient's body for characterizing select structures and disturbances within key organs. Other advances include genetically engineered antigen labels for accurately identifying destructive organisms, and precisely configured synthetic analogues of metabolic agents with high specificity for triggering select defensive responses.

These technologies will continue to grow exponentially as health care becomes increasingly important to a relatively wealthy, but rapidly aging society. Indeed, a significant barrier to advances in health care is their cost, which grows faster than the general inflation rate. Additionally, knowledge of how to apply available advances in real practice settings is limited. Despite dramatic technological advances in many areas, management of several common functional disorders (such as dyspepsia, irritable bowel syndrome, chronic fatigue syndrome, and fibromyalgia) has not substantially improved. Patient dissatisfaction with conventional medical management of these common disorders has fueled huge expenditures of personal health dollars for alternative care, much of which remains of uncertain benefit and risk.

Inadequate physician time for optimal patient care. Health care costs have risen steeply and, with physician time a valuable commodity, few clinicians can spend more than a fraction of an hour-even with new patients. In the past, a patient's expectations were largely inspired by the image of a house-calling physician who devoted hours of personal "bedside" attention to every patient, a model seldom found today. In many environments physician time is so limited as to preclude a comprehensive evaluation. Inattention to detail or inadequate assessment of the patient's overall biopsychosocial situation can generate inefficiencies of care.

The challenge of patient assessment: nonspecific and overlapping symptom patterns. More than 30% of the population experience functional disorders that cause symptoms without any corresponding organic pathology. The clinical challenge is to appropriately recognize these functional disorders and discriminate them from less common cases of organic disease that require specific therapy. One barrier to efficient clinical evaluation is that the symptom patterns of organic disease and functional disorders are surprisingly nonspecific; for most visceral disorders, there is only a weak correlation between a given symptom complex and underlying organic disease. For example, only 10 to 20% of patients with classic "peptic ulcer" symptoms have ulcers and many patients with ulcers are asymptomatic or present with other than classic symptoms. Another barrier is that patients presenting with acute or chronic functional disorders or organic disease may have multiple symptom complexes that overlap. Overlapping symptoms are the rule; they confound the diagnostic process and obscure organic disease that requires specific diagnosis and/or therapy.

Patients must be primed to understand the features of their symptoms and essential medical terms so that they can provide a diagnostically-relevant history. The rapid-fire questions of a rushed physician interview do not allow time for most patients to understand the issues and think through their answers. When patients are rushed or feel as if they are not listened to, anxiety mounts and the outcomes of care deteriorate.

Extracting a history from patients, especially in the face of overlapping problems, requires diligence, skill, and time. However, conventional logic assumes that the non-specificity and overlap of symptoms obviates benefit from a detailed history. In addition, the process of unraveling an adequate history takes time and the expectation that the process will yield valuable clinical information. Furthermore, the onslaught of technology has displaced history taking and symptom pattern recognition, rendering these skills underutilized and unrefined for most physicians. For these reasons, an adequate history is rarely obtained. When physicians are not clear on symptom presentation and basic pattern recognition, they are driven to perform more tests, use more medications, or refer patients for consultations, procedures, or even surgery. Accordingly, costs escalate and the efficiencies of care are lost.

Physician information overload. Sophisticated new technologies provide a volume and complexity of diagnostic information that can easily overwhelm practicing clinicians. Few physicians can effectively manage and utilize advanced equipment, space age therapeutic regimens, and the massive amount of information that goes with them. Ironically, health care providers are even overwhelmed with the process of handling medical records for patients. Paper charts are outmoded, especially in poly-physician environments where there is rarely the time to carefully read complex and often poorly organized charts. Sophisticated electronic medical record (EMR) systems have been developed to handle laboratory records and other patient information. However, available EMR systems do not (1) collect and process information from patients, (2) transmit patient data to physicians, or (3) manage historical data regarding the physician-patient interaction (patient history, physician assessment, follow-up data) in a dynamic, efficient manner. The inadequacies of current patient data management systems disrupt the process of care.

Patient information overload and lack of self-care. Like clinicians, patients encounter information overload. Typically, a patient is provided with information regarding their problems and possible treatments in technical jargon that leaves them bewildered and intimidated. The information that should clarify the nature of their problem becomes an almost insurmountable barrier to understanding. In addition to being incomprehensible, health instructions and treatment plans may also be impractical for an individual patient's lifestyle, and thus will not encourage compliance. Thus, the patient becomes alienated from their potential role in the care process, leading to a poor response to treatment.

Failure to capitalize on patient-centered care. Although patient outcomes and the efficiency of care will be improved by an integrated approach to the whole patient and the physician-patient interaction, conventional medicine perseveres in its biomedical focus on disease, tests and medications. Notwithstanding rapid technological advances in medicine, the patient's initial psychological status and response to the therapeutic process plays a substantial role in the overall success of treatment. The highly variable, but well-documented "placebo response" reflects the inherent role of patient health attitudes and the quality of the physician-patient interaction on the patient's response to therapy. The potential benefits of patient-centered elements of the care process (Table 1) are evident, but they are difficult to implement in most busy, resource-limited practice settings. (Reference: Stewart, M., J. B. Brown, W. W. Weston, I. R. McWhinney, C. L. McWilliam, T. R. Freeman, and K. A-Kaila. 1995. Patient-centered medicine: transforming the clinical method. Sage Publications, Thousand Oaks, Calif. 117 pp.)

Controlling costs while preserving quality of care. As health care costs have skyrocketed, many cost-saving solutions have been explored in the health care marketplace. Per capita costs have been cut to preserve profits, jeopardizing health outcomes and the quality of care. The challenge is to ensure that the quality of and access to care are maintained and improved, while costs are contained. Health care managers must make difficult decisions when attempting to control costs while preserving the quality of care. There is great potential for waste through misapplication of care on one hand, or under-utilization of indicated treatments on the other.

The process and outcome data needed for cost-saving, quality-preserving decisions. Disease management guidelines have been developed in an attempt to standardize care and control costs. However, methods are not available to appropriately test, implement, and monitor specific disease management guidelines that have been developed in an effort to control costs while maintaining the quality of care. Decisions regarding allocation of health care resources generally rely on available data for treatment efficacy in study populations. However, these efficacy data often fail to predict the treatment effectiveness in real practice settings. The information needed to make decisions regarding health care utilization are data from real practice settings on patient outcomes (how the patient felt and functioned before and after treatment), the process of care (what the physician did and thought), and the costs. Health care providers do not have the time to verbally gather or record process and outcome data. Paper questionnaires are also an impractical and inefficient means to gather high quality data. Therefore, the health care delivery system currently lacks the tools to measure the impact of treatment on the outcomes and quality of care. Practical systems are needed to routinely perform these essential measurement tasks.

The predicate for the present invention is informed by the problems inherent in the current health care delivery infrastructure cited above. It is with recognition of these problems in the state of the art that the present invention provides the following objects.

OBJECTS OF THE PRESENT INVENTION

The ecumenical object of the invention is to develop an integrated computer system that supports a new paradigm of health care delivery. The system, referred to herein as the Comprehensive Patient Management ("CPM") system, will accomplish this goal by integrating biomedical and psychosocial approaches to patient management and providing tools to improve and measure patient assessment, quality of life, and physician process. These approaches and tools will provide a means to support the delivery of high quality health care at lower overall costs.

The specific objects are:

to provide a computer system (the patient module) to improve the effectiveness of patient assessment by collecting standardized, comprehensive data during an interactive patient interview session. The CPM system efficiently and accurately collects patient information, such as presenting complaints and relevant psychosocial factors, and identifies provisional problems. The system also collects and stores measures of patient outcomes (the change in patient quality of life between initial and follow-up evaluations).

to provide a computer system (the physician module) to facilitate physician process and simultaneously capture measures of physician process in the database.

to provide a system that is user-friendly for both patients and physicians so that the system is practical for installation in provider organizations that deliver care in ambulatory settings.

to provide a system that implements and monitors patient-centered care in practice settings.

to provide integrated measures of patient outcomes and physician process that can be utilized to investigate the success of specific treatments and overall management strategies.

to provide a server/database for dynamic, problem-oriented archiving of the data collected by the CPM system and efficient access to that problem-oriented information.

to provide a patient management system that is flexible. This flexibility will allow continued refinement in assessment and treatment strategies and can be expanded to manage the variety of medical disorders (Table 2).

TABLE 2

Initial Modules for Screening and Characterization of Specific Conditions (partial list)

Gastroenterology
Cardiovascular medicine
Pulmonary medicine (chronic lung disease, emphysema, asthma)
Infectious disease
Allergy
Rheumatology/Orthopedics/Rehab Medicine (joint, back and connective tissue conditions)
Renal disorders (hypertension)
Endocrine disorders (diabetes, thyroid conditions, obesity)
Male genitourinary: Urology (prostate conditions)
Female disorders: Gynecology (dysmenorrhea, female conditions)
General Internal Medicine (general health status, preventive medicine, functioning in activities of daily living)
Neurology (headaches, strokes, epilepsy, movement)
Psychology (psychologic conditions and stress)

SUMMARY OF THE INVENTION

Figure 1:
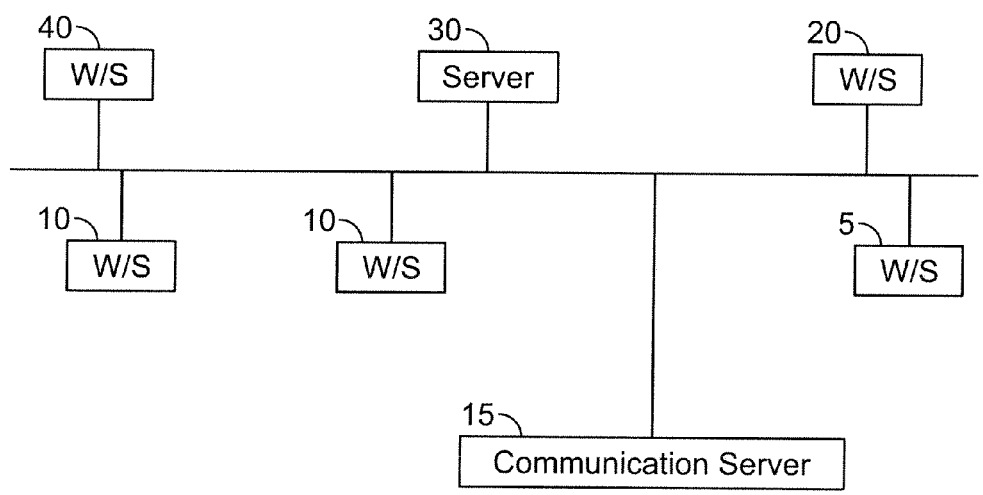
FIG. 1 is a hardware block diagram of the salient components of the present invention.

Overview of the comprehensive patient management (CPM) system. The computerized CPM system provides a practical means to implement, integrate, and measure biomedical and psychosocial approaches to comprehensive patient management in real practice settings. This integration is embodied in the basic components of the invention, namely a patient module, a physician module, and a server/database (FIG. 1). Each of these module implements a computer program, software subroutine, a group of computer instructions, or the like. The overall goal of the invention is to maximize quality while controlling health care costs. This goal can only be achieved when the background problems raised above are addressed.

Patients interact with the inventive system during the initial assessment sessions, at exit interviews, and upon clinic revisits. Patients (or family or caretakers) directly input data into the patient module, a user-friendly, interactive computer system that systematically records and analyzes relevant information about the patient's health. These structured, comprehensive data are then efficiently processed and reported to physicians in a problem-oriented format to facilitate patient assessment and diagnostic decision-making. Physician process is aided by expert medical assessment and treatment strategies that are embedded in the inventive system. The physician edits the report and adds assessment and management plans, which are then generated as the final clinical report. Finally, the physician may also select patient educational materials, which are given to the patient along with a health summary at the exit interview session. CPM "remembers" patients upon return and updates their symptom profiles accordingly. The system saves time and improves efficiency for both patients and physicians by focusing the health care encounter on active problems. Changes in patient quality of life and response to and satisfaction with care, captured in the server/database, can be related to specific treatments and the overall management process.

Ultimately, methods of the inventive system facilitate high quality, cost-effective patient care by supporting clinical investigation of specific treatments; testing, implementation, and monitoring of management guidelines; and integrated quality of care assessment and improvement. The CPM system entails use of separate screen and script files to provide an extremely flexible, scalable instrument for physician-editors who design the clinical strategies. Screen files contain the requisite information to generate displays that present text, question sets, and multimedia presentations. Script files control the flow of patient-CPM interaction and the visual presentation of information. The goal of system development is to use a computerized system to embody the process of a master clinician in patient assessment and physician management. Computerization of this process requires ongoing refinement as this system is expanded to cover a wide range of medical disorders.

Accurate, thorough patient assessment. The first component of the invention is the patient module, which is designed to increase the effectiveness of patient management by accurately assessing the patient's presenting health problems. A fundamental concept underlying the development of the invention is that collecting accurate, comprehensive patient data enhances the efficiency and effectiveness of patient assessment, thereby improving patient outcomes and ultimately providing data to guide appropriate utilization of health care resources. A structured, computer-assisted interview with sophisticated branching capabilities is used to present an intelligent and relevant sequence of questions to patients and collect standardized data. The structure of the CPM system permits direct entry of input data by a patient at a CPM patient carrel or other compatible computer platform. These data are then analyzed in real time using a sophisticated system for implementing Boolean logic, based upon expert-determined criteria for identifying symptom complexes and provisional problems. Using this mechanism, the system can discern multiple and overlapping problems.

Patient-friendly interface and communication strategy. The most important feature for patient-friendly performance is presenting patients with simple, straightforward, unimodal questions. In addition to presenting questions that patients can understand, it is essential to offer options that cover the range of possible responses so that patients are not frustrated by having to choose among inaccurate or incomplete responses. As detailed subsequently, strategies are also implemented to minimize patient confusion by clarifying any potential relationship among multiple symptoms. These features increase the accuracy of the data collected by ensuring that the patient is neither confused by the questions nor limited by inadequate response options.

It is also essential to keep the system relevant to the patient. Triage questions are asked to highlight areas of immediate concern to the patient and screening questions are presented to cover key health issues. Branching algorithms focus further questioning on details pertinent to the patient. To maximize patient involvement and relevance, interactions with the system are individualized based on prior patient responses and patient characteristics (e.g., age, gender, ethnicity, socioeconomic background).

A simple, interactive graphic interface directly gathers data from patients and implements patient-friendly performance that is rewarding, fun, and intuitive-even for computer-naive patients. Multimedia elements (e.g., images, sound, video clips, and animation) are used to present questions and educational material and make the system more visually appealing. To assure that the process is easily understood, patients are frequently given feedback or instructions based on their answers. Specific patient responses are used to construct grammatical phrases or complete sentences of concatenated text strings. This concatenated output is used to provide the feedback and instructions mentioned above and to confirm the accuracy of data and the effectiveness of communication with the patient. The audio system plays pre-recorded audio files on cue or uses voice synthesis to read concatenated output, which patients listen to with headsets or speakers. Voice input can be recorded so that patient comments are captured in context. To further simplify use, exemplary patient carrels are equipped with touchscreen monitors so that use of a keyboard or mouse is not required. However, the patient module can be adapted to run on any IBM-compatible or Apple platform equipped with a mouse and keyboard and/or a touchscreen.

Capture relevant patient outcomes for common disorders using quality of life measurement. Assessing the quality and consequences of the treatment process requires quantifiable endpoints. For common disorders in outpatient settings where serious outcomes (morbidity, hospitalization, surgery and death) are infrequent, the clinically-relevant endpoint is patient-reported quality of life. To this end, after provisional problems have been identified and confirmed with the patient in the interview process, the inventive system measures condition-specific quality of life. Quality of life measurement focuses on the frequency and severity of symptoms and disruption of function and activities of daily living, and forms the basis for assessing patient outcomes. Although quality of life endpoints may appear soft, measures have been validated for both general and condition-specific health status. CPM will develop, rigorously validate, and implement reliable and practical quality of life measures, which are critical to assessing and improving the outcomes of care.

Patient exit and revisit interviews assess response to treatment process. During clinic visits, patients initially undergo the computerized CPM interview session and are then evaluated by a physician. Finally, the patient returns to the patient carrel for an exit interview, to receive a personalized health summary, instructions for self-care and follow-up, and educational materials. The patient's response to the physician encounter is sought, focused on the effectiveness of communication and understanding of the physician's diagnosis and plans for testing and treatment. When the patient returns to clinic, CPM operates in a revisit mode, reconstructing prior symptoms and problems, assessing compliance with medications or other recommendations, eliciting patient response to therapy and other changes in symptoms, quality of life or health status, and collecting patient questions and concerns. These exit and revisit sessions provide a unique opportunity to further understand the natural history of common medical problems and assess the patient's response to physician process, specific treatments, or overall management strategy.

The impact of dissecting overlapping conditions on efficient patient assessment. When a patient presents with a single problem, the inventive system collects data on key symptom features (Table 3) that usually determine the general nature of the problem. When multiple problems exist, the system presents simple questions about key features to discriminate discrete symptom patterns. Without this careful history, the diagnostic process is confounded. As patients interact with the system they are primed to provide as accurate and complete data as possible.

TABLE 3

Key Features of Symptoms

Localization and referral
Quality and description
Time pattern (onset, duration, time of day, and frequency)
Precipitating factors: relation to meals, bowels, exercise, posture TABLE 3-continued Key Features of Symptoms Relieving factors: relief with rest, bowel movements or passing gas, or with food, antacids or antisecretory agents
Change in any of the above A problem-oriented approach provides the structure that the invention utilizes to unravel overlapping symptom patterns from clinical, measurement and investigational perspectives. Whereas overlap obscures symptom patterns, disaggregating a patient's symptoms by the key features allows common symptom patterns to be identified. For efficient diagnostic process, multiple, potentially overlapping problems must be discerned so that evidence of serious illness is not obscured by common functional problems (e.g., muscle aches or common functional bowel problems).

Dissecting overlap is also crucial to promptly detecting changes in symptom patterns, which can provide early evidence of new disease processes. Furthermore, patients commonly get in a habit of recognizing all sensations from their chest as heartburn, and from their abdomen as gas. When something changes, the patient may associate new symptoms with these familiar entities, thereby precluding a clear history. Unless patient self-awareness is promoted and adequate time and skill are focused on dissecting these changes, important diagnostic clues may go unrecognized.

This process might seem overwhelming, but there are only a finite number of symptom groups. Furthermore, discrimination of these groups can be straightforward when the patient is appropriately educated and the process is approached methodically. During the patient interview, the patient is educated regarding key features and overlap. Simple questions are asked about key features of symptoms elicited during screening. The invention is designed to encompass the nonspecific and overlapping nature of common symptom patterns, detect symptom groups and changes in patterns, and recognize when presenting symptoms fall outside of these common groups. The data collected facilitate discrimination of underlying organic disease from common functional patterns. This approach benefits individual patients by enhancing management. The broader public health benefits of this approach will be reaped when data on large volumes of patients are analyzed and used to refine clinical assessment strategies.

Facilitating physician process. Several elements of the invention support efficient and effective physician process. These elements include improved quality of patient data, presentation of patient data in a problem-oriented, clinical report format, generation of a problem-oriented clinical report that can be readily edited by the physician, and efficient, problem-oriented access to relevant patient data. After the CPM patient assessment, physicians are provided with patient data in a format that allows them to confirm the nature of the underlying problems and effectively pursue the appropriate steps in clinical management. A menu with options drawn from treatment guide-lines facilitates physician management decisions. Because of the inventive system's modular design, guidelines can be customized for clinical investigation or specialized applications. Alternatively, clinical guidelines in use at provider sites can be installed into the inventive system. Due to system capacity for collecting a comprehensive medical history, flagging and prioritizing important problems, and facilitating reporting and ordering, the physician will have more time available to devote to patient-centered care issues.

Incorporating patient-centered care into routine practice. A computerized strategy, implemented at both the patient and physician modules facilitates patient-centered care. This strategy includes a variety of functions, such as enhancing physician-patient communication; educating and activating (priming) patients to provide an accurate history; clarifying and transmitting patient's health questions and illness concerns to the physician; assessing the patient's health attitudes; and collecting comprehensive biopsychosocial data. The psychosocial screening assessment examines several domains, including physical symptoms that may represent somatization, life events that are perceived as stressful (e.g., relation, financial, and work-related stress) and psychologic co-morbidity (e.g., depression or anxiety states). The invention is designed to support incorporation of patient-centered care into routine practice by integrating these patient-centered elements into the overall management process and assessing the value of these interventions.

Several mechanisms serve to increase the likelihood that the physician attends to patient-centered care issues. At exit and revisit interviews, the various aspects of patient-centered care are evaluated and related to data on physician process. Issues relating to patient-centered care, such as psychosocial factors, health attitudes, illness concerns and questions, are presented to the physician as provisional problems. These patient-centered aspects of care are implemented in anticipation that they are important determinants of the response to therapy and overall outcomes. In other words, when patients are empowered to take an active role in their own care, outcomes will be improved and costs reduced.

Implementing a problem-oriented approach to patient assessment and information management. The inventive system uses dynamic, problem-oriented strategy as the basis for patient assessment, facilitating physician process, and provider access to patient records. In accordance with this concept, the Joint Commission for Accreditation of Healthcare Organizations (JCAHO) requires problem lists for all patients. However, conventional methods for generating and maintaining a clinically-relevant problem list for each patient add to physician workload. Due to marginal benefits from this increased workload, physician compliance is poor.

The inventive system analyzes standardized patient assessment data for symptom patterns that comprise appropriate provisional problems. A provisional problem list is formulated, confirmed with the patient, and then presented to the physician at the outset of the patient evaluation session. The physician reviews the provisional problems, modifies them as appropriate, and assigns a working or final diagnosis. Upon revisits, the system provides efficient access to prior patient data and simplifies updating of problem-oriented patient information.

Positive and negative criteria for symptom patterns are used to define provisional problems. These criteria are implemented in a flexible format that allows for continual refinement as experience is gained.

However, physicians are given control over problem designation. They can edit problem names, combine, or separate problems as the clinical picture unfolds. Identified problems are linked to management algorithms; following problem identification, diagnostic and treatment options are presented to the physician for selection or modification. The problem management strategies can be customized for various practice settings or applications, such as incorporating management guidelines adopted at specific provider sites, conforming to the practice patterns of individual physicians, or implementing randomization protocols for controlled clinical trials.

Clinical applications of process and outcome measures. Integrated measures of physician process and patient outcomes from real practice settings, as captured by the invention, provide powerful measures of the human, social, and financial impacts of routine medical care. The invention provides practical tools to collect consistent, reliable data on patient assessment, patient outcomes, and physician process. Using these integrated data, the invention supports rigorous clinical investigation of specific treatments. The system also provides a practical means to test, implement and monitor disease management strategies in real practice settings. Lastly, the generation of linked process and outcome measures provides a unique mechanism for integrated quality assessment and improved management of common disorders in outpatient settings.

Efficient patient management requires adapting management strategies to the attributes of individual patients. Appropriate diagnostic and treatment interventions differ drastically in population subgroups, such as the elderly, children, or women of childbearing age. To this end, the invention accommodates real-time adaptation of communication strategies, question sets, and management algorithms for patient characteristics, including age, gender, socioeconomic and educational background and medical history. Since the occurrence of many diseases varies with patient characteristics, particularly age and gender, individualized management strategies will be more cost-effective than broad-spectrum approaches for all patients.

Database/Server. Both the patient and physician modules are linked to a database which captures raw patient data (initial clinical assessment, quality of life and response to therapy), provisional problems, patient verification of the identified patterns, physician process (observations, impressions and treatment), the final clinical diagnoses, and long-term follow-up. Using standard communication protocols, the invention can query other electronic medical records systems to obtain other patient data, per patient costs and utilization of health care resources, laboratory data, consultations, surgeries, and pathology. Utilities will be provided to monitor data integrity, prevent duplicate records and safeguard data security and patient confidentiality.

Modular System Design. The inventive system uses a modular design to support efficient development, refinement, and expansion of the interview process and clinical strategies for health care management. A separate screen editor and screen files are used for developing screen content (questions and other displays). A separate script editor is used for developing a script file. The script file controls the patient interview process, specifically the display of screens for the patient, application of logic for branching, report generation and problem recognition, and data collection and reporting. A third component, a presentation engine, interprets the script, displays the screens, and executes the actual presentation process. This modular design supports expansion of the system to handle integrated management of a wide range of medical disorders (Table 2), thereby enhancing the utility and value to physicians, patients and provider organizations. With a modular design, physician-editors can create and refine the questions, other displays, and the clinical strategy without reprogramming the system code itself. The modular design allows the accumulated knowledge in the database to be translated into continuous refinement of these algorithms.

The system and strategy will be adapted for a wide range of computer platforms, networks, and Internet applications. The modular design supports applications for the full range of provider organizations as well as individual patients seeking to better understand their symptoms or guidance regarding health care options.

DETAILED DESCRIPTION OF THE INVENTION

The Structure and Function of Basic System Components

FIG. 1 depicts the salient components of the present invention as it resides in the medical clinic environment. The system employs a network of client-server computers, with individual workstations for accessing system programs and providing select services. The patient carrel 10 is equipped with a PC-based computer (IBM-compatible or MAC), typically Pentium class, and is linked to the network (two are depicted in FIG. 1). These workstations are programmed to communicate with the central support server/database 30 to provide the requisite functionality to patients and physicians, as will be discussed in more detail below.

In addition to the patient carrel 10, the admitting clerk is equipped with a workstation 5 for entry of select, patient-specific information that serves to open a patient record for this clinic visit and generate data entries or updates for the server/database 30. For example, the admitting clerk collects or confirms simple biographical information (e.g., address and phone number).

Continuing with FIG. 1, a nurse utilizes workstation 20 for entry of vital signs (temperature, blood pressure, pulse, and weight), that are generally taken during each clinic visit. These data are added to current visit data entries and stored in the database. Using prompting screens, the nurses also collect the patient's chief complaint (why the patient has come to clinic) and determine whether any emergent situations exist. Provisions are also made for direct entry of data regarding presenting complaints and potentially emergent problems.

Finally, the physician workstation 40, typically placed in the examining room, operates to provide the physician with CPM problem-oriented patient evaluation and historical information and management guidelines. Physician workstations communicate with the CPM server/database 30. In addition the CPM clinic system can utilize the communication server, 15, to interconnect with the provider's central electronic medical record system to upload clinical reports or obtaining patient data. In addition, the CPM system can connect with third party systems, such as insurance companies via network, Internet, or modem applications. The system also includes a centralized data warehouse/server that can serve Internet or modem applications from distant sites for the purposes of accessing patient records, research, quality assessments, and benchmarking performance.

Figure 2:
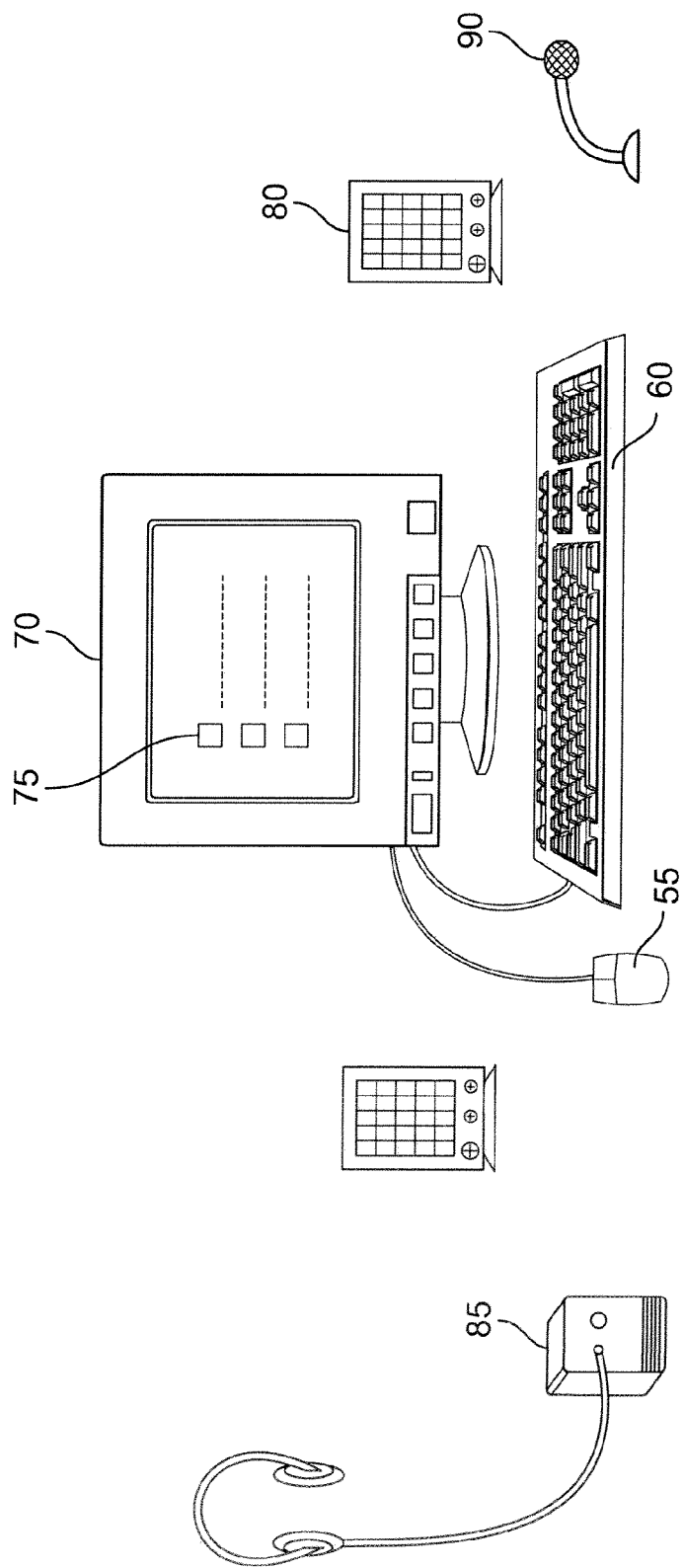
FIG. 2 is the hardware configuration of the patient carrel.

In the exemplary mode, patients use a patient carrel 10 (FIG. 1) in a private cubicle near the waiting room to directly input their responses to questions regarding symptoms and psychosocial issues. This patient carrel is typically configured as depicted in FIG. 2, comprising a display terminal 70 for presenting questions and other information and a touch-sensitive screen, which has icons 75 and text to guide the patient through the assessment module. In addition, the system has the capacity to record patient comments via microphone 90, and an option for speakers 80 or a headset and volume control 85, to allow the patient to listen to voice synthesized or previously recorded questions and text. Further optional input means include mouse 55 and keyboard 60.

The Flow of Information for Patient Assessment and Physician Process

Figure 3:
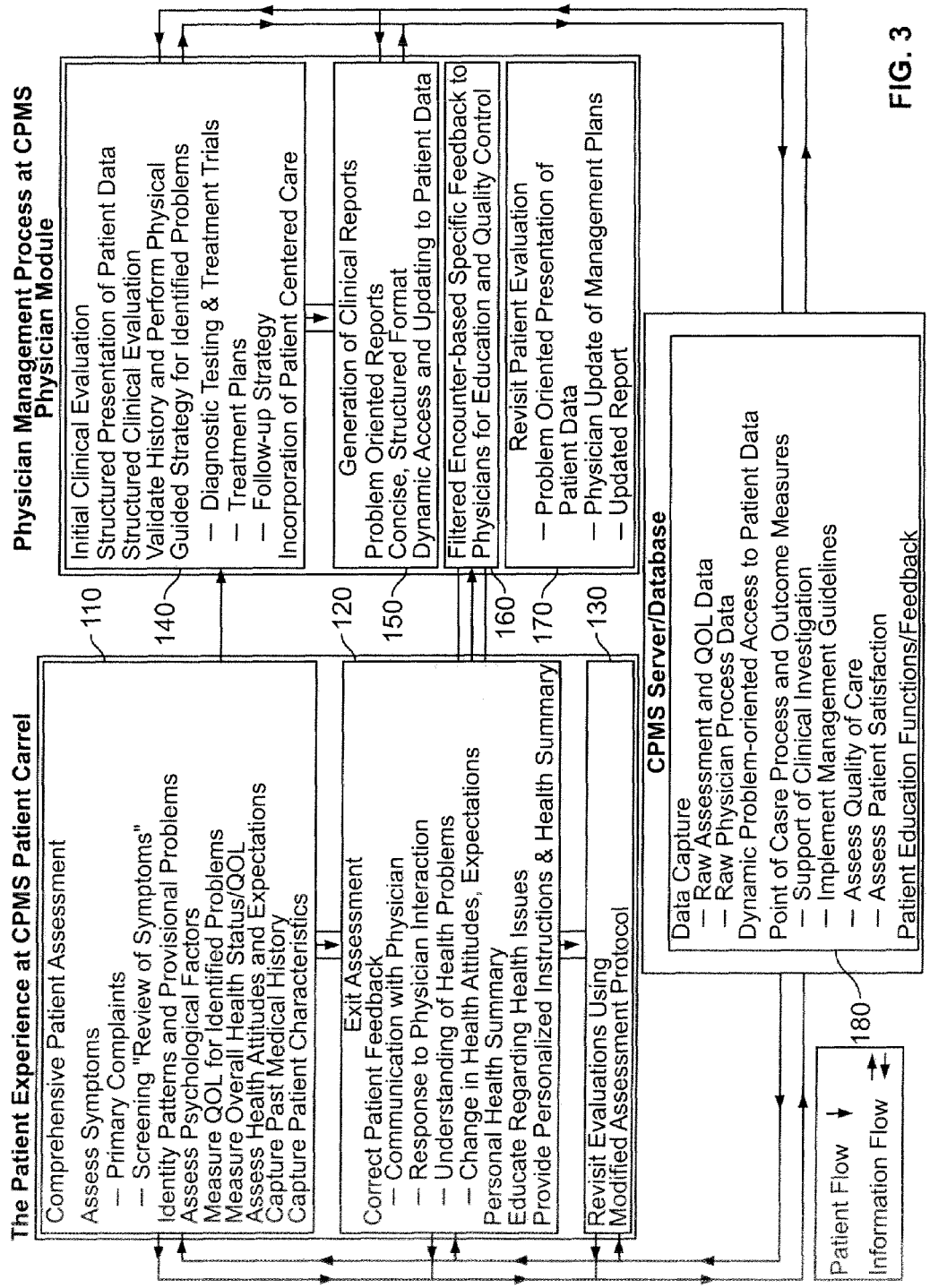
FIG. 3 is a flow chart for the the CPMS-implemented CAPM, showing how the information flows through the various components of the invention.

The patient experience and information flow through the system is depicted in FIG. 3. Patient sessions at the patient carrel are illustrated on the left side: the initial CPM assessment before seeing the physician, 100; an CPM exit session after the physician evaluation, 110; and a CPM revisit evaluation, 120. The issues addressed during the initial and exit sessions are highlighted in FIG. 3 (100 and 120, respectively). Upon returning to the clinic, the patient undergoes a revisit evaluation at the patient carrel, followed by a physician visit and an exit session. The protocols for these revisit sessions will be modified from those outlined for the initial and exit sessions, as described subsequently. For each of these sessions, bi-directional information exchange occurs with the CPM server/database, 180. The system queries patient information necessary for conducting the session and patient data, problem summaries, and concatenated reports are sent to the server, 180.

Activities and information flow at the physician module are illustrated on the right in FIG. 3. At the outset of the initial patient evaluation, patient data summarized from the patient CPM session are presented to the physician in a problem-oriented format. The physician module guides the physician through consideration and editing of the patient data, 140, thereby validating these data. The physician can also input other assessment data (e.g., other problems or physical findings), select management options, and select patient education materials. The final report is completed, 150, based upon these data generated from the patient CPM session, as edited by the physician. Depending upon system setup in the provider environment, the physician will receive filtered feedback from the patient exit session, 160, regarding the patient's understanding of what was communicated and their response to the process. For the revisit session, 170, the physician will be presented a problem-oriented summary of the initial problems and interim status collected by the invention. The server/database, 180, supports both the patient evaluation and physician session and captures data from these sessions.

System Use in Practice Settings

Figure 4A:
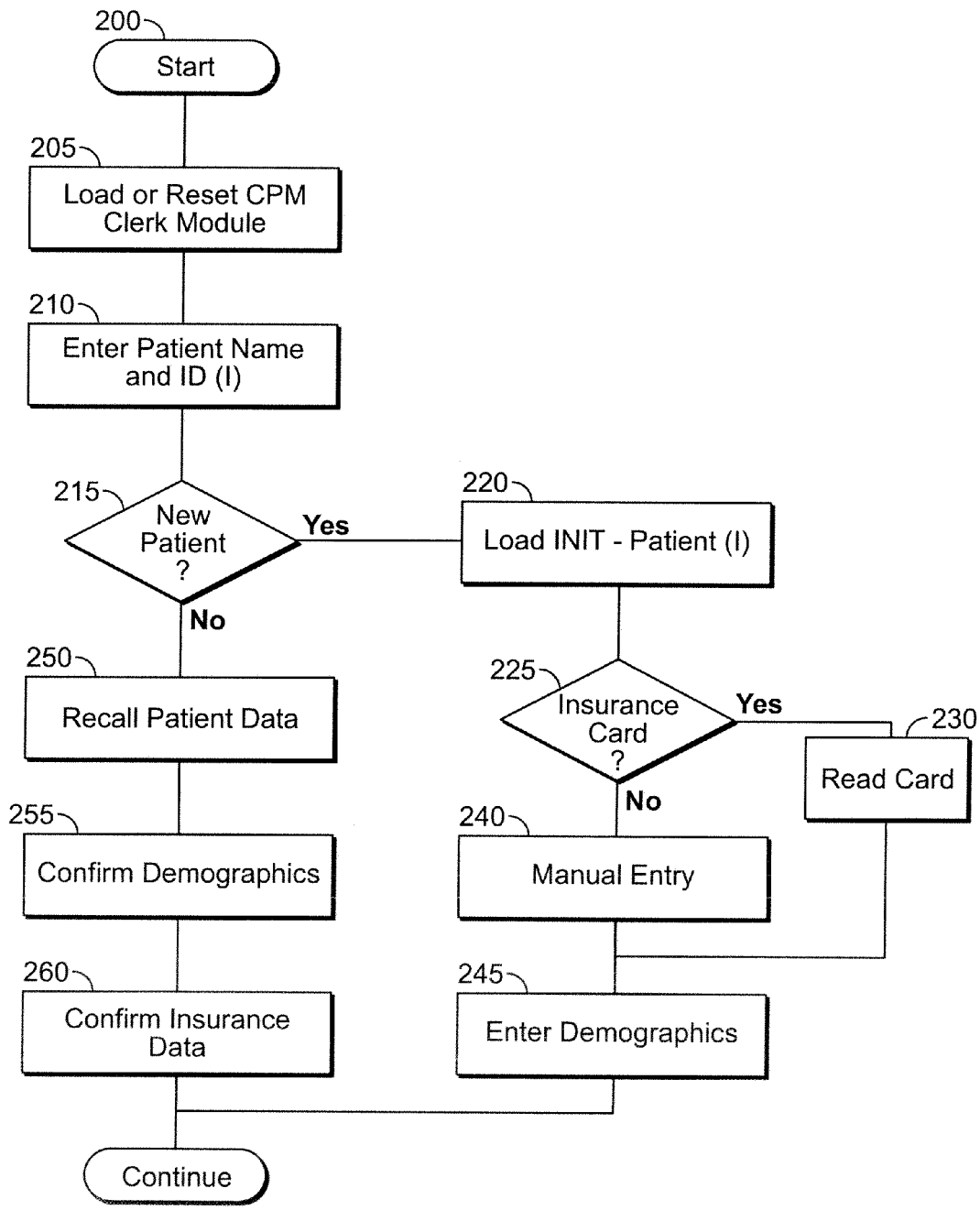
FIG. 4A is a flow chart of the patient sign in and nurse assessment program.

Patient sign-in and nurse assessment. Turning to FIG. 4A, system operation is generally initiated when the patient signs in with the clerk. The clerk starts the CPM system, 200, and loads the clerk's module or resets the system for another patient, 205. The clerk enters the patient's name and identification, 210, and the system queries the server/database to determine if prior records for this patient exist, 215. If yes, logic branches to block 220 and the system presents screens for input of patient information by the clerk, 220. At test 225, the system determines if the patient has a pre-programmed insurance card (e.g., Smartcard) for simple downloading of information into the CPM file. If yes, logic branches to block 230 and the card data are extracted and placed in the patient record. If no, the clerk manually inputs data, block 240. Basic biographical and demographic data are then entered by the clerk, 245. If at test 215 the patient is found to be revisiting the clinic, logic branches to block 250; prior patient data is read into memory and displayed on the clerks screen for confirmation of demographics, 255, and insurance data, 260.

Initial triage of patient complaints. Continuing with FIG. 4B, the patient is then escorted to the nurses or clinic coordinator workstation where the system is started or reset for the new patient, 265, the nurse/coordinator module is loaded, 270, and vital signs are entered, 275. The nurse then enters the chief complaint (the reason or reasons why the patient has come to clinic), 280, and responds to the questions and answers, 285, regarding whether this is an urgent situation. These questions probe for problems such as a new onset chest or abdominal pain, bleeding or shortness of breath that might reflect serious heart, lung or gastrointestinal disease. If the answers indicate a situation that warrants immediate attention by a physician, yes at test 290, the patient is escorted to the emergency or urgent care facility or the case immediately reviewed with a physician. An option is also available for this initial input of information (steps 200 to 290) to be conducted at the patient carrel by a single clinic worker. Alternatively, the system has an option for the patient to initiate the session without outside guidance.

Figure 5A:
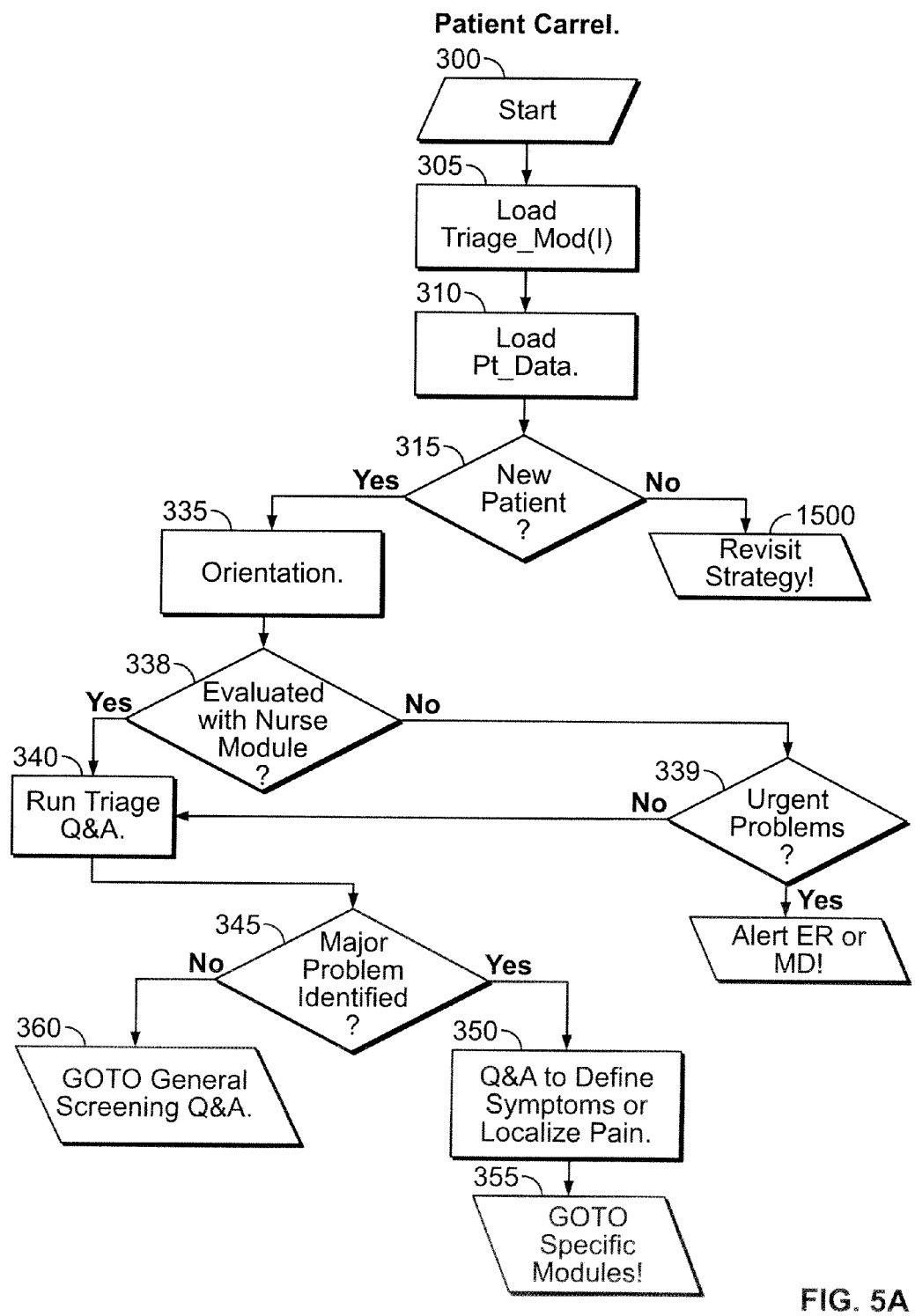
FIG. 5A is a flow chart of the program run on the patient carrel.

In the exemplary mode, patients will be escorted to the patient carrel to begin testing (FIG. 5A). Logic conceptually begins at block 300 with starting and loading of the CPM triage module, 305. Following system access, the initial data collected from the admitting clerk and nurse are loaded into active memory, block 310. Logic continues to determine whether the patient is new to the system, test 315. If the patient is new to the system, a multimedia tutorial in CPM system use and the evaluation process is presented, 335. This education package will be adapted to the patient's characteristics, such educational background.

Figure 13:
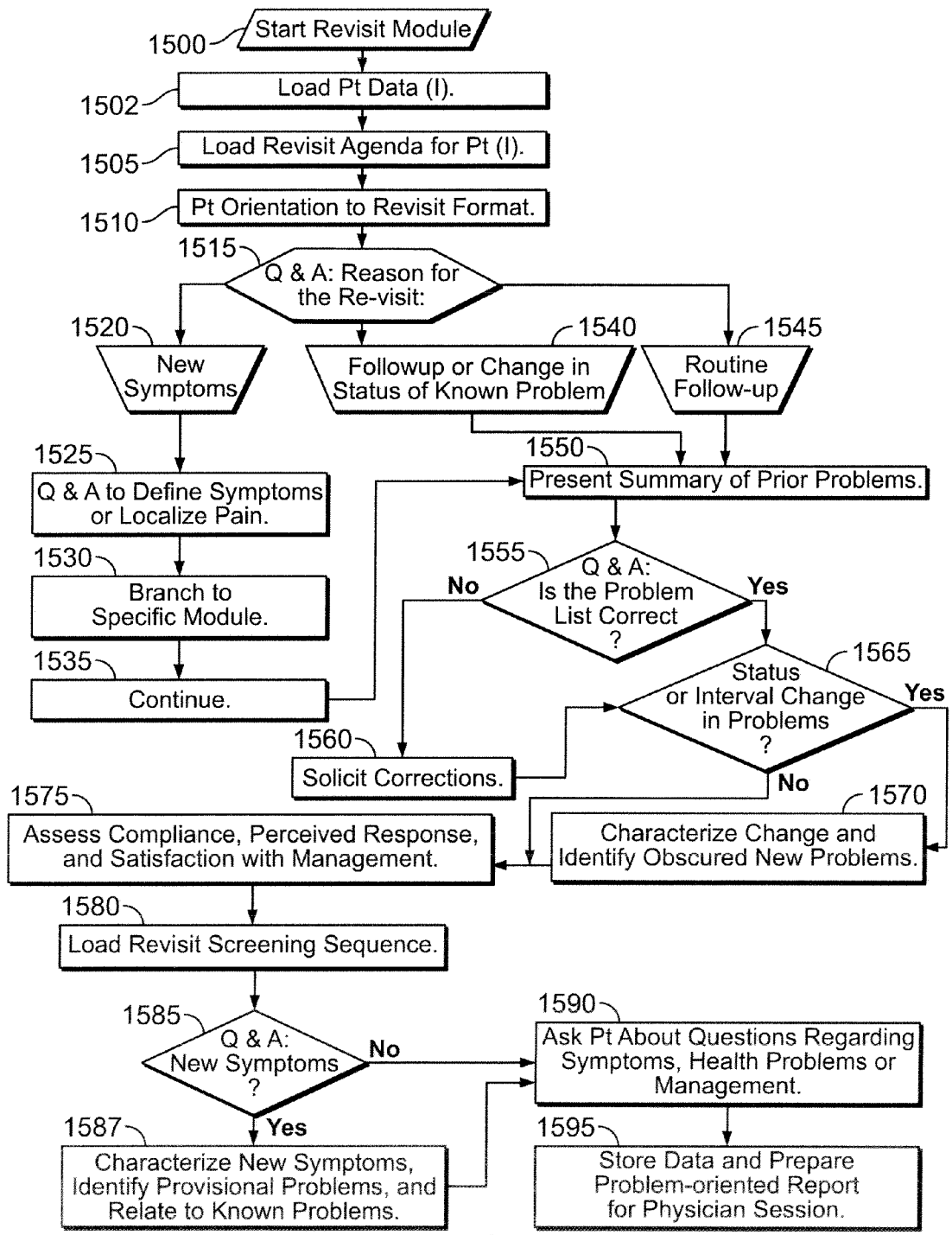
FIG. 13 is a flow chart of a program for functions and flow of the patient module during revisits by the patient.

If at test 315 the patient is known to the system, the existing file on the patient is recalled for a revisit protocol, block 1500 (FIG. 13).

Figure 4B:
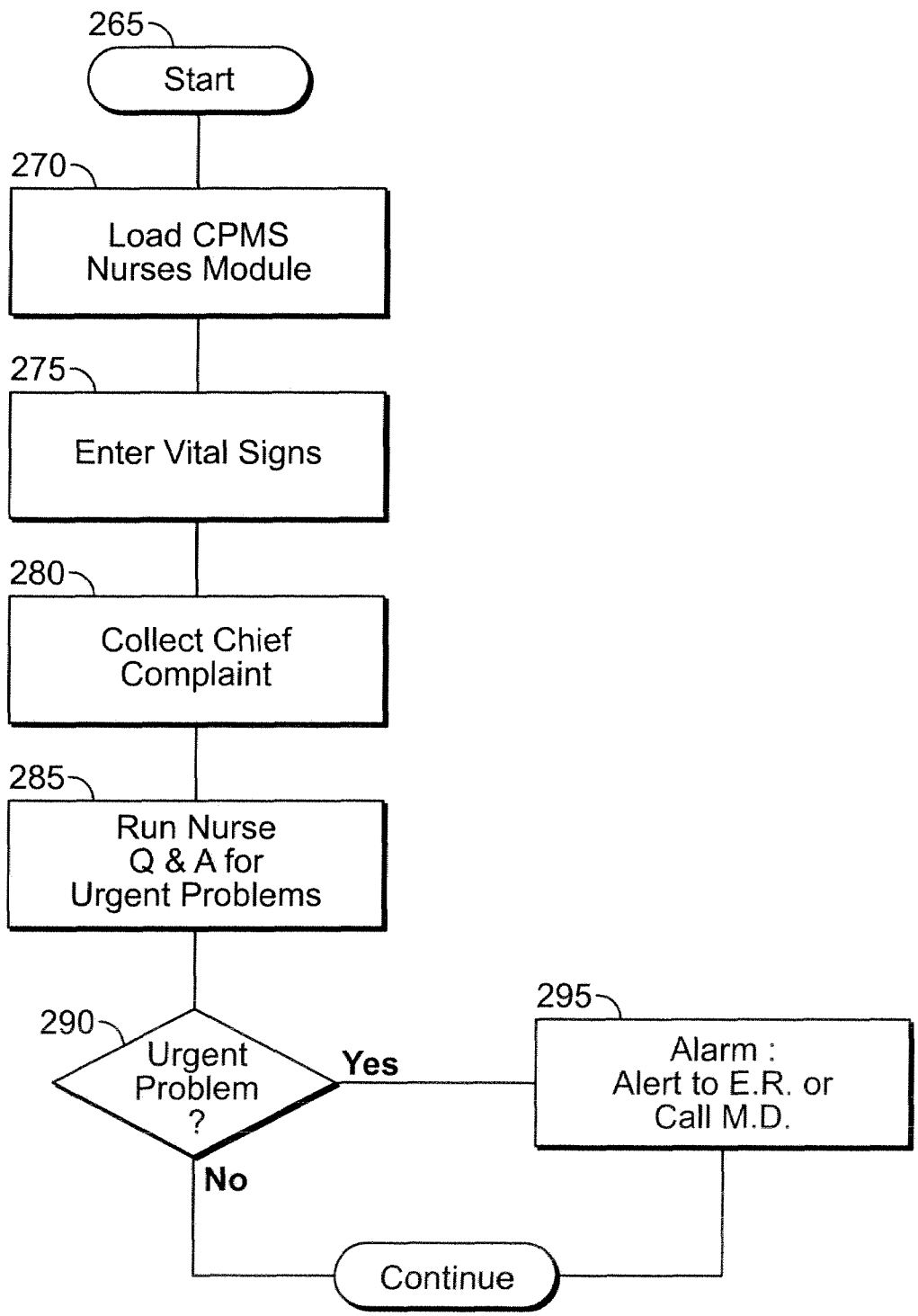
FIG. 4B is a flow chart of the program run on the nurse's module.

If the system is operating without a nurse (No at test 338), the next sequence determines if the patient requires immediate medical attention and then obtains the primary purpose of the patient's visit. These questions, block 339, are adapted from the nurse module, (FIG. 4B, blocks 275-285). If concerning symptoms are found in this mode, an alarm is activated to call clinic staff and the evaluation is terminated.

The next order of business is a sequence of triage questions, block 340. This initial triage obtains structured data regarding the principal reasons that bring the patient to clinic, thereby informing the system where to being asking more specific questions. In the triage screen 340, patients are asked whether they are presenting with pain, discomfort, or other symptoms (e.g., dizziness, coughing, bowel problems, or ankle swelling). Patients are also questioned about other health care issues they want the physician to review. If a major problem is identified at block 345, more detailed questions are presented to further define the symptoms or localize the pain, 350. These triage data allow appropriate branching to specific modules to characterize these problems of central importance to the patient, 355, before returning to complete screening questions. If the patient is presenting for routine follow-up or does not have new symptoms, then screening questions are asked, 360, as illustrated subsequently.

Assuring accuracy in patient assessment. Three approaches are used to increase and monitor the accuracy of patient answers:

1. Question screens can be set so that at least one answer is required. When the patient attempts to advance to the next screen, a message box appears instructing them to make a choice if the patient has neglected to provide at least one answer.

2. On most question screens, a final response is included that is exclusive of the other answers (e.g., none of above). If the patient checks the final response plus any of the mutually exclusive responses, then a message to correct the answers is generated as the patient pushes the screen advance button. If the patient does not correct the answer, then the process is interrupted and clinic staff are alerted to attend to the problem.

Figure 5B:
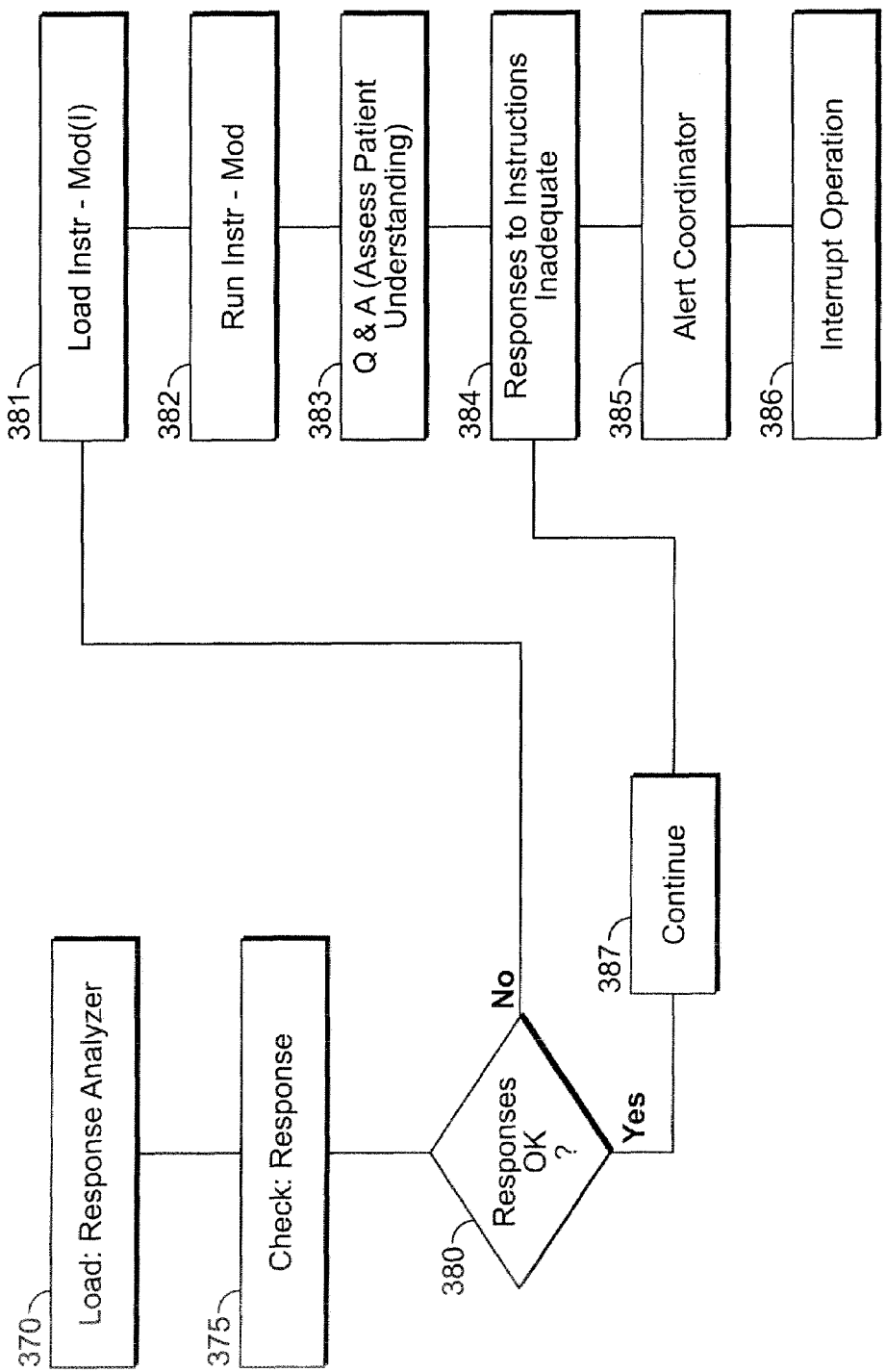
FIG. 5B is a flow chart run of the program run on the general screening module.

3. Finally, a system response analyzer is loaded during patient assessment at block 370 (FIG. 5B) and operates in the background to track inconsistent responses. The response analyzer detects responses that reflect either a failure in understanding the nature and operation of the system or a patient uninterested in participating in the process. The response analyzer checks the patient's responses after each question set, block 375. If the responses are acceptable, block 380, the system continues at block 387. If responses indicate a problem exists, an instructional sequence is loaded at blocks 381-382 and runs to inform the patient of the nature of the problem and proper system use. At block 383, questions are asked to determine if the patient understands the problem and the instructions. If the response is acceptable, the process is continues at block 386. If not, clinic staff is alerted and the program is interrupted, blocks 385-386. Since the accuracy of patient responses is critical, patient understanding is tested early in the interview process by embedding several questions with potentially inconsistent responses. Conflicting responses are monitored by the response analyzer as described above.

This process also reveals system problems due to inadequate instruction or confusing displays or questions, which will be continually revised by either CPM consultants or trained clinic personnel. These mechanisms provide a means to rapidly identify patients whom are having trouble with system operation, understanding questions, or maintaining interest in continuing the interview.

Figure 5C:
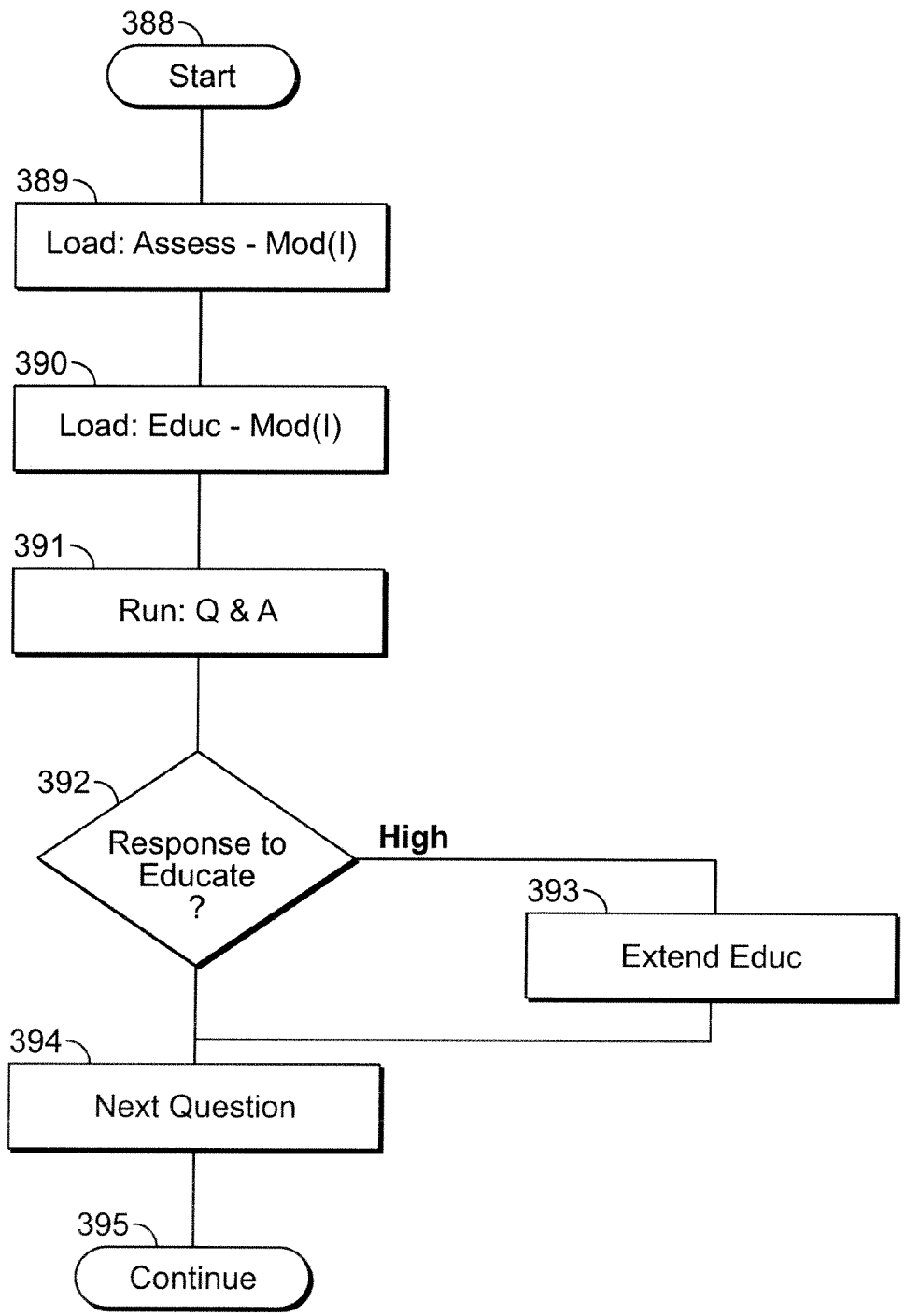
FIG. 5C is a flow chart the education module relevant to the upcoming topic.

In addition, at selected point in the interview process, such as the beginning of a new question block, the system loads an education module relevant to the upcoming topic (FIG. 5C, block 388). This education module helps the patient understanding the terms and issues they need to be informed about to accurately answer questions. Continuing with FIG. 5C, the system presents the specially crafted question and answer sequence to the patient, block 391. In accordance with system instructions for that module, periodic educational clips are provided, and the patient is requested to assess how helpful these clips are in increasing their understanding and enjoyment of the process. Questions will also determine patient understanding of the material that is presented. At test 392 these responses to the educational elements are evaluated. If the response is positive, the system branches to block 393 and the patient is given the option for extending the educational module. In either event, the question and answer sequence continues to completion, block 395, when the patient has covered the material.

A new paradigm for informed consent. An example of numerous potential applications of this modular system in a clinic setting is provided. In the exemplary mode, an interactive module that includes educational sequences and evaluation questions will be developed for collecting informed consent of patients. Applications include informed consent for routine procedures or surgery as well as for clinical investigation to meet Institutional Review Board requirements for human subjects. To improve patient comprehension, this module incorporates video clips and audio and visual aids so that appropriate information is conveyed to the patient regarding the intervention they will receive. Because the information presented can be catered to patient characteristics, appeals to a variety of learning styles with its multimedia format, and can be reviewed or repeated at the patient's pace, this sequence provides an effective means for education on informed consent issues. Evaluation questions and internal system checks (described above) assess the patient's level of understanding of the material presented. When this sequence is completed, the patient's consent can be given online or a printed form can be generated for the patient to sign. For clinical studies and trials, this method of gaining informed consent is particularly valuable due to its capacity to transmit general information on the risks and benefits of study participation, as well as to avoid contamination by catering specific information to control and intervention groups. Standardized presentation and evaluation of informed consent issues can reduce legal costs and risks. The CPM computerized informed consent module also yields substantial cost-savings because of reduced need for staff to conduct informed consent activities.

Figure 5D:
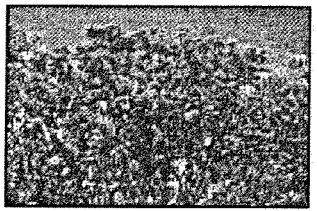
FIG. 5D is an example of the questions and answers asked.

Variable text functions. Sophisticated variable text functions provide patient-specific descriptions for each symptom (e.g., "your pressing, mid-chest discomfort" or "your burning upper abdominal pain that comes on an empty stomach"). These individualized descriptions are used to introduce screens, questions, or responses, so that the patient is clear regarding the question being asked and the symptom that is referred to. This serves to ensure simplicity, clarity, and efficacy of patient-system interactions. Screens depicting this strategy are presented in FIG. 5D.

Figure 6:
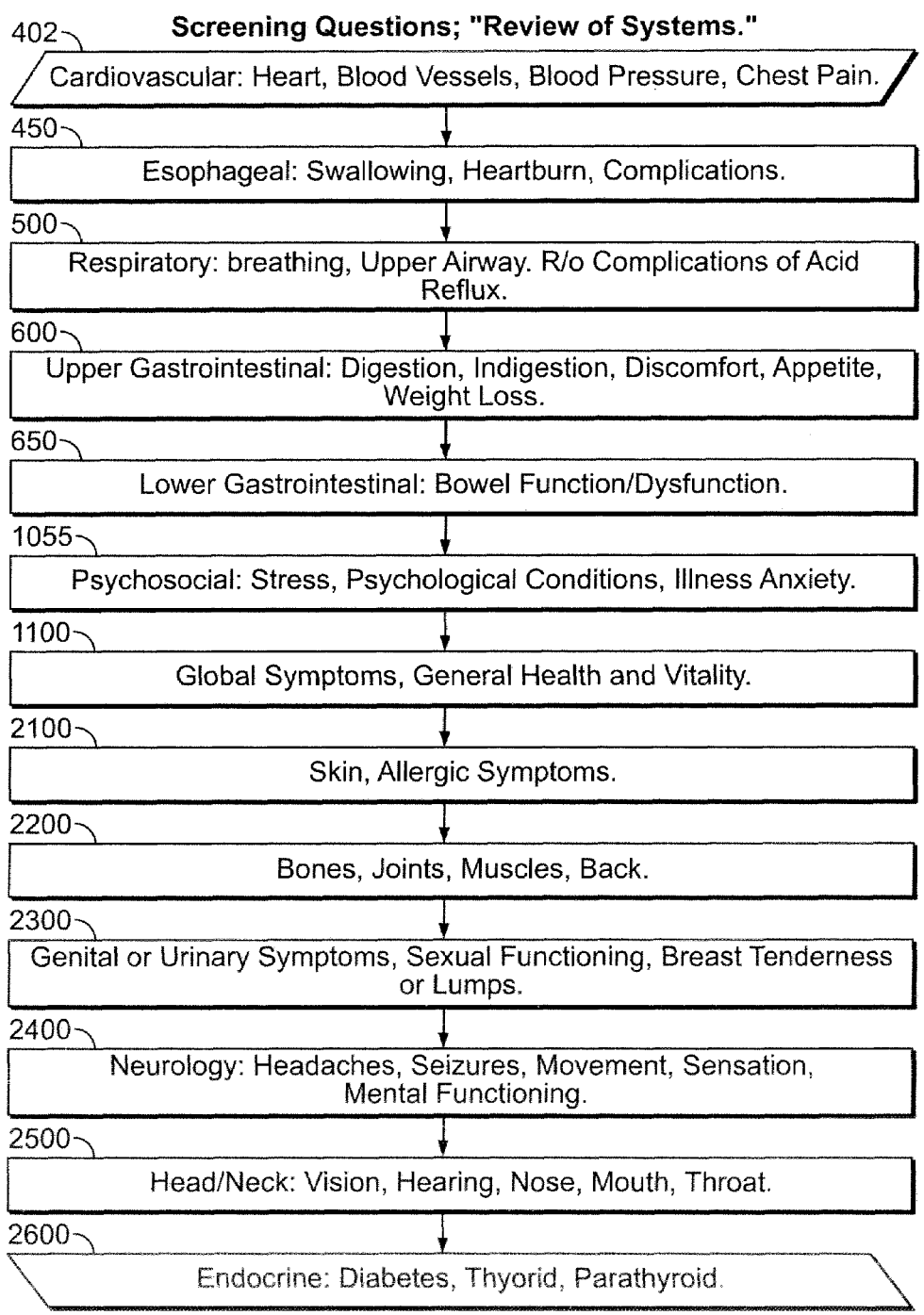
FIG. 6 is a flow chart of the program relating to the screening questions; "review of systems" that are given to the patient to answer.

Overall screening strategy. The next sequences involve implementation of a thorough clinical evaluation to pursue symptoms elicited in the triage module. To fully elucidate these problems, all of the screening questions are asked pertaining to the index complaint. Branches with more detailed questions are pursued as appropriate. After questions relating to the primary complaint are asked, comprehensive screening is performed to assure that potentially important symptoms are detected and characterized. The system is designed to encompass common disorders encountered by all medical and surgical subspecialties and to facilitate a thorough clinical evaluation. Therefore a complete history, known as a "review of systems", is obtained (FIG. 6). To support this task, the CPM system includes modules for each area of medicine (Table 2) that are crafted by leading clinicians in these subspecialties. The first seven of these screening areas are described (FIG. 6); the remaining ones are not considered.

Strategies are implemented to minimize patient confusion that might arise when patients are asked in detail about one symptom before they are clear how it relates to their other symptoms. To minimize this problem, initial screening questions are designed to establish a road map for potentially related or overlapping symptoms. In addition, the screening sequence is designed to identify probable symptom complexes. For effective diagnosis, it is not sufficient to know whether the patient has a chest discomfort or an abdominal pain. Enough information must be collected during screening to determine the possible nature of the pain: for example, a chest pain with exertion and an abdominal pain that is relieved with bowel movements. With these pieces of the puzzle, the variable text functions of the invention allow reference to the specific symptoms that have been elicited thereby allowing specific questions that can clarify the relation between symptoms. This strategy is particularly important when patients have multiple complaints, which is the rule rather than the exception.

Figure 6A:
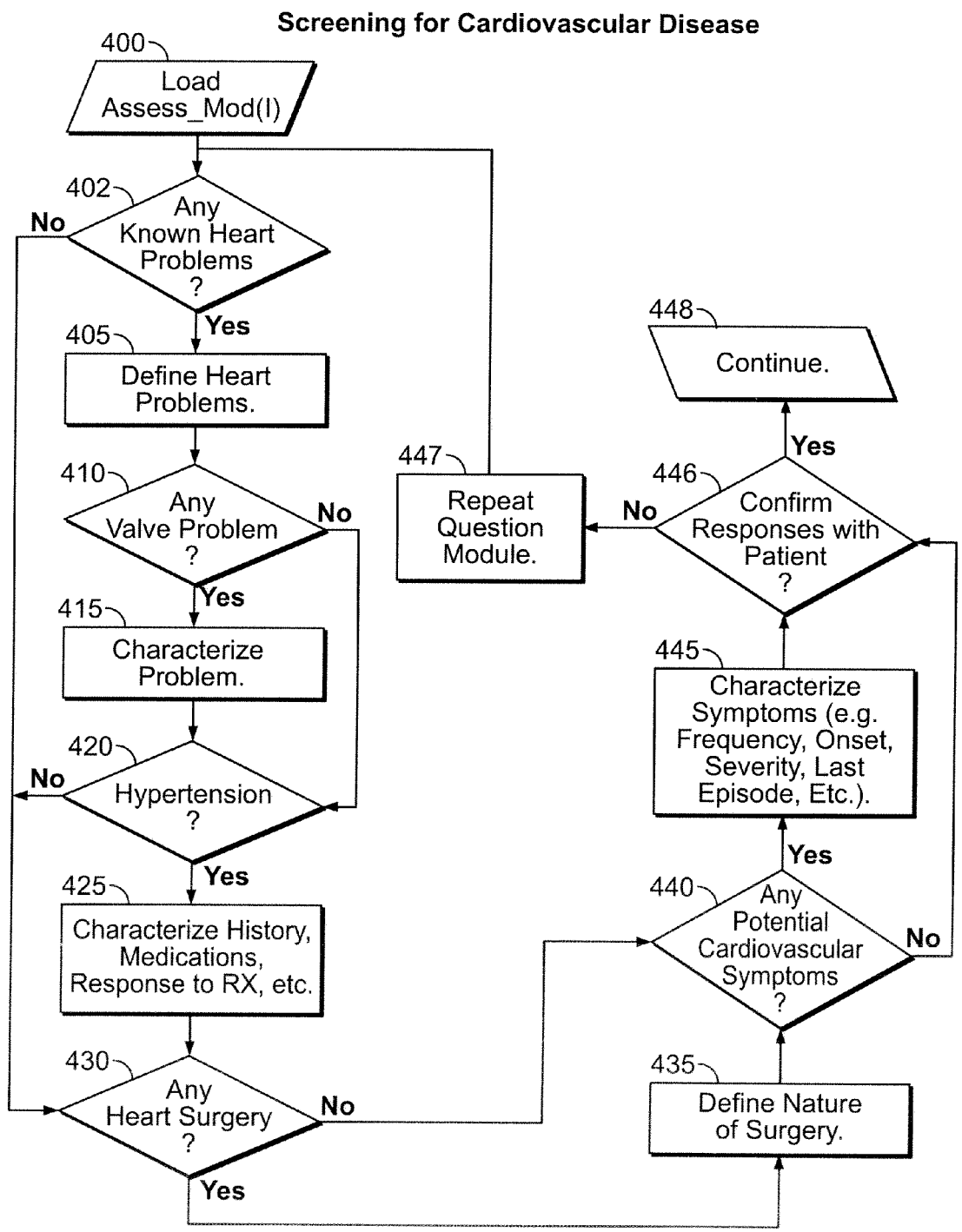
FIG. 6A is a flow chart of the program that screens for cardiovascular disease.

Two general points on the screening strategy warrant emphasis:
1. Branching is utilized so that detailed characterization is only pursued if screening questions are positive.
2. At the conclusion of a brief sequence of screening questions, patients are presented with a grammatical, narrative summary of positive and negative symptoms for them to confirm or reject, block 446 (FIG. 6A). If rejected, block 447, the patient returns the screens where responses need to be changed. After the patient accepts the summary, they continue onto the next question set, block 448. This sequence is repeated for every block of questions and will be denoted in subsequent figures by the phrase "confirm and continue." The information collected during the more detailed characterization of symptoms is also confirmed in a similar manner.

The strategy for screening includes features to minimize patient frustration that would otherwise result when attention is focused on common symptoms that do not really trouble them. Matrix screens are used for certain common symptoms, such as heartburn or constipation, so patients have the option of indicating how frequently they are troubled with the problem (e.g., never, rarely, some, a lot, always) (FIG. 6.1). In addition, at the outset of detailed questioning, patients are given a chance to indicate whether a problem is of a minor nature and given the option to skip detailed questions. However, all symptoms are reported to the physician, grouped by priority either patient judgment or system criteria (see below).

Screening strategy for heart, lung, and gastrointestinal problems. To implement the logic described in the above section, the first round of screening questions is designed to identify important cardiac, respiratory, and gastrointestinal symptoms at the outset of the interview. These three modules are also called up for symptoms that appear cardiac, pulmonary and gastrointestinal in nature, since each of these systems must be evaluated for problems in any one of them. Assessing chest and abdominal symptoms poses a common and often challenging task for physicians, since symptoms in these regions are often nonspecific, multiple, and overlapping. Psychosocial assessment screening is also included because of its general importance. The other modules that are not illustrated follow a similar strategy to clarify symptom presentation.

Figure 6B:
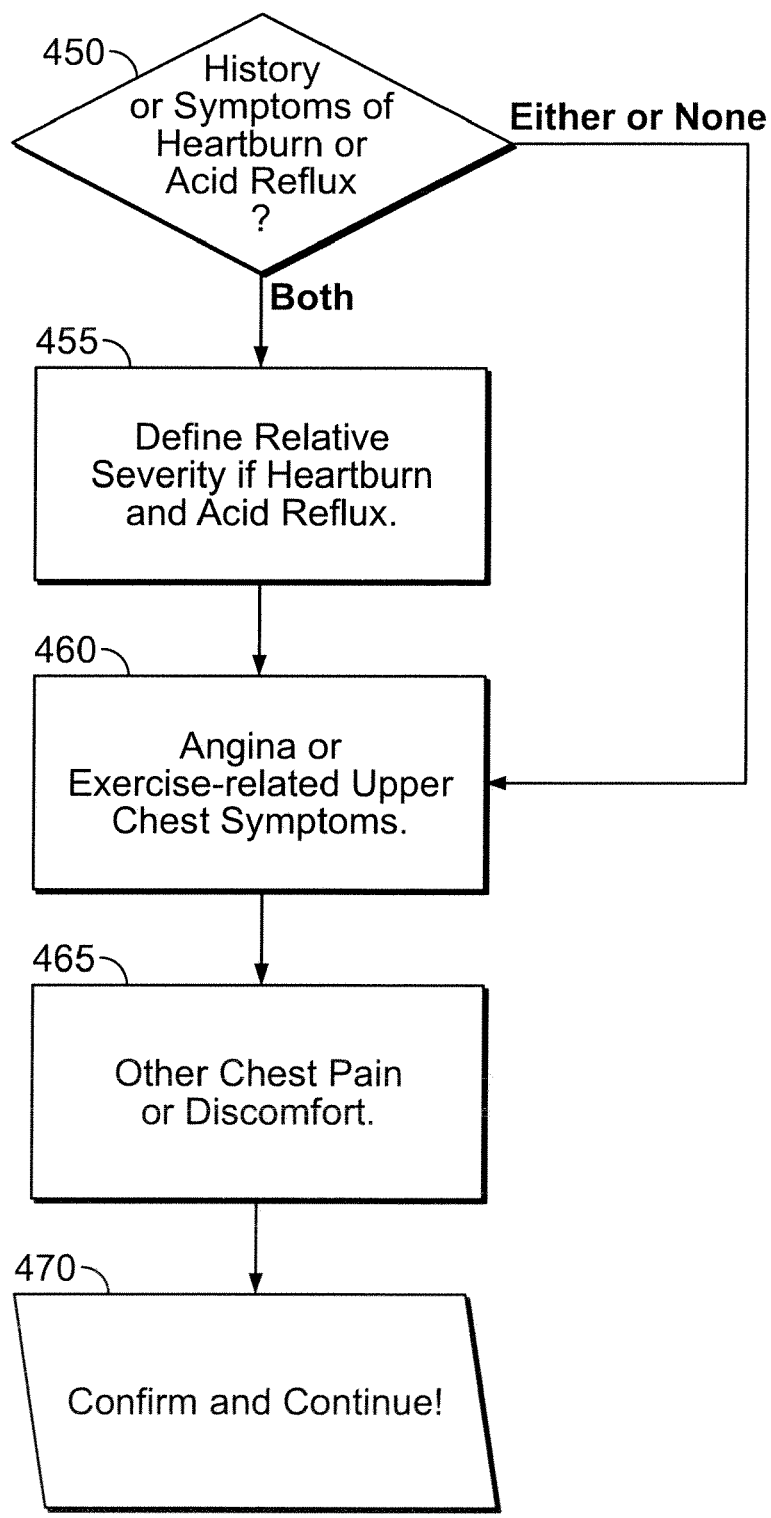
FIG. 6B is a flow chart of the program that screens for acid reflux and chest pain.

At block 400 (FIG. 6A), the assessment module is loaded for the review of systems and characterization of common disorders and configured for the patient based on the initial information collected and data available from previous visits. The first screening questions address a history or symptoms suggesting heart, valve, or rhythm problems (FIG. 6A, blocks 402 through 440). Continuing with FIG. 6B, a history and symptoms of heartburn or acid regurgitation are sought. The patient is then asked about angina or exercise related symptoms and any other chest complaints, blocks 460 and 465. For each question, the variable text function is used to remind patients of their prior answers, so as to avoid confusion.

Figure 6C:
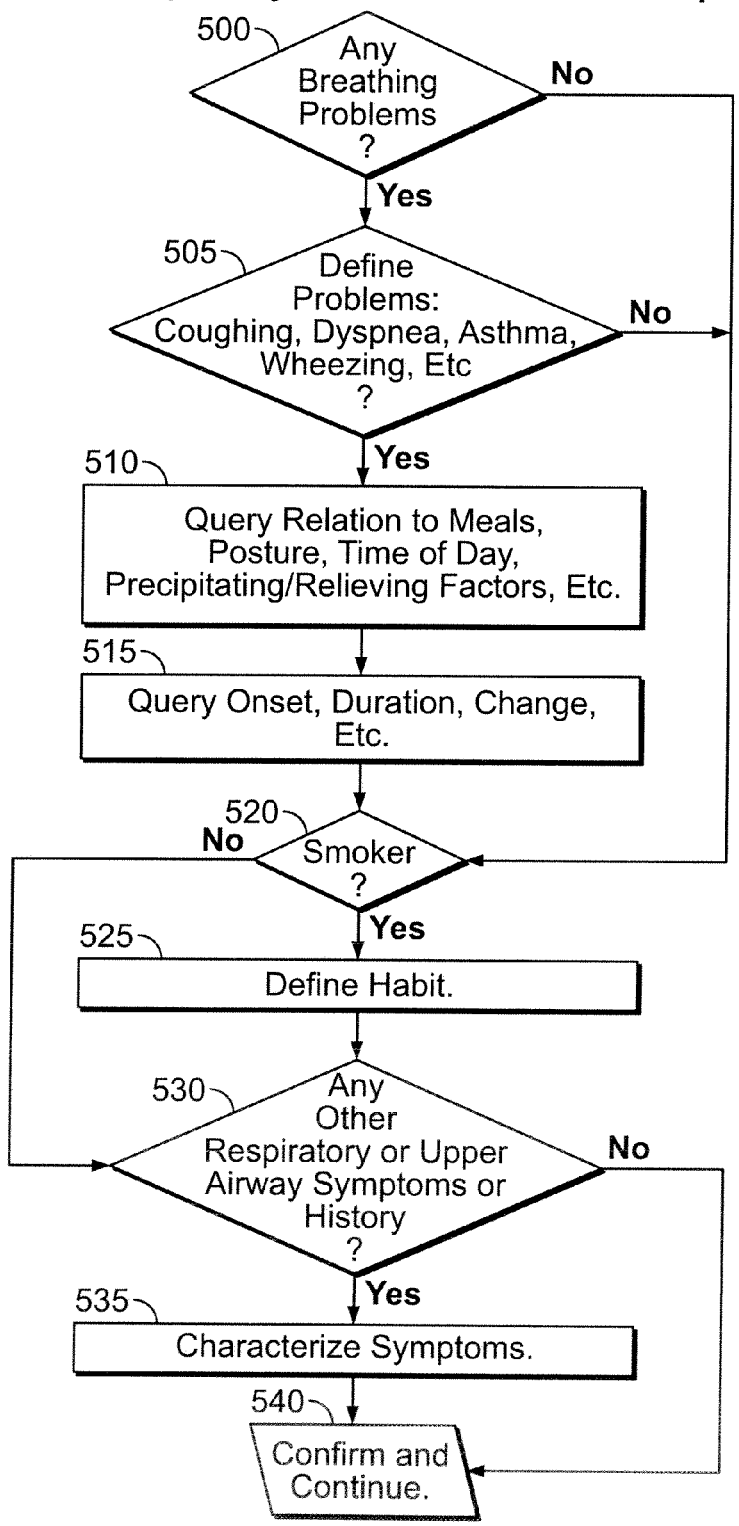
FIG. 6C is a flow chart of the program that screens for respiratory conditions & GER complications.

Screening questions for respiratory conditions are then presented (FIG. 6C), asking about coughing, choking, shortness of breath (dyspnea), and asthma, blocks 500 and 505. Positive responses are pursued, characterizing key diagnostic clues, such as the relation to meals, posture, and time of day, block 510. Onset, duration, and change in pattern are then sought, as appropriate, block 515. Other respiratory and upper airway symptoms (e.g., sneezing, coryza, sore throat, and hoarseness) are also sought and characterized in blocks 530 and 535. If a patient has multiple respiratory complaints they are asked if these symptoms are separate or related. If a patient reports that different symptoms (e.g., cough and shortness of breath) follow the same pattern, then only one set of characterization questions is presented.

Figure 6D:
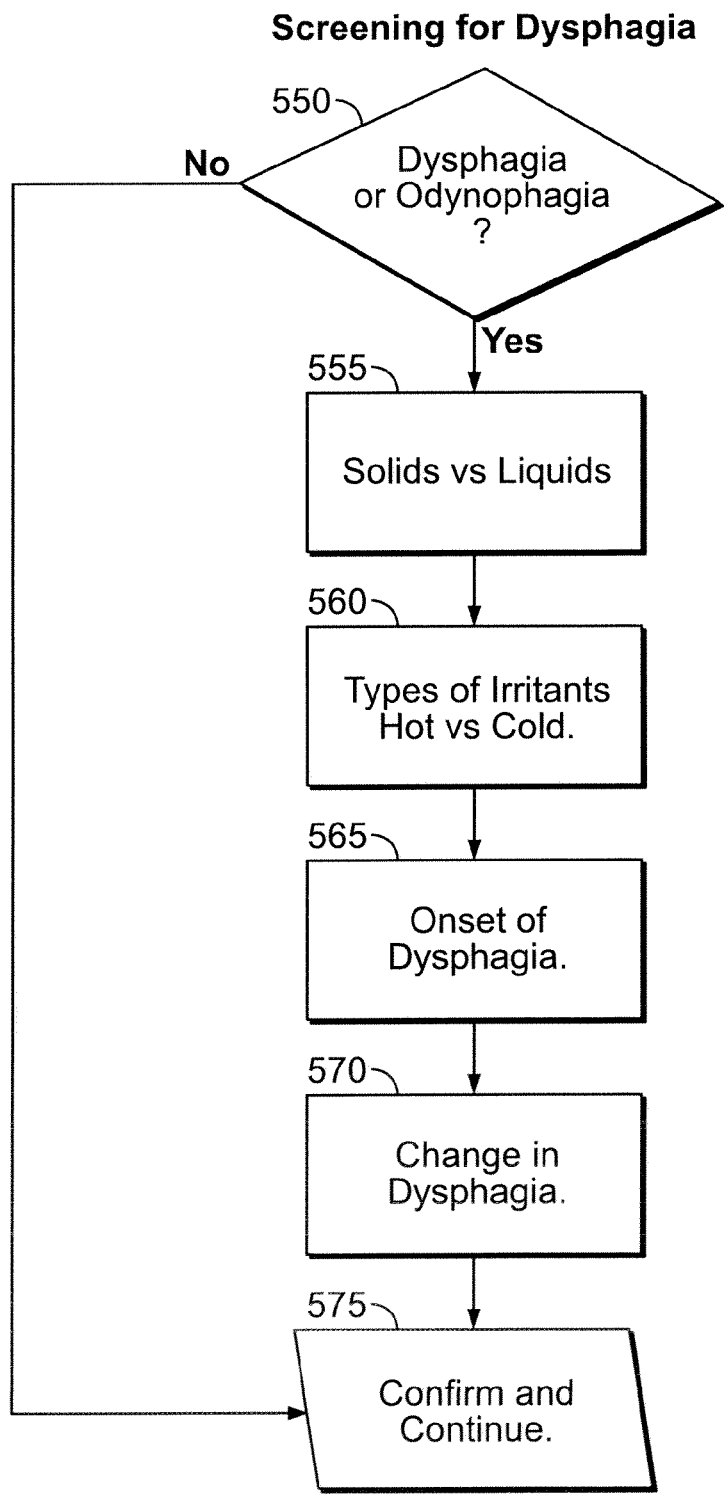
FIG. 6D is a flow chart of the program that screens for dysphagia.

In FIG. 6D, the process continues to address pain or difficulty with swallowing, block 550. If positive, symptoms are characterized, focusing on key features that are clinically valuable for distinguishing symptom groups. For example, difficulty swallowing with solids (block 555) that is of recent onset (block 565) or progressive in nature (block 570) raises concern about a constricting lesion in the esophagus. This would be flagged for the clinician in the CPM patient assessment report. On the other hand, if the problem is characterized by difficulty with both liquids and solids that is intermittent and not progressive, this is typical of esophageal spasm and would be reported as such. Subtle clues such as discomfort upon swallowing with cold, hot, or irritating liquids (e.g. citric juices) can be very helpful, suggesting an irritable, rather than an obstructed esophagus (block 560). The invention implements Boolean logic to capture and recognize these clues to identify important symptom complexes.

Figure 6E:
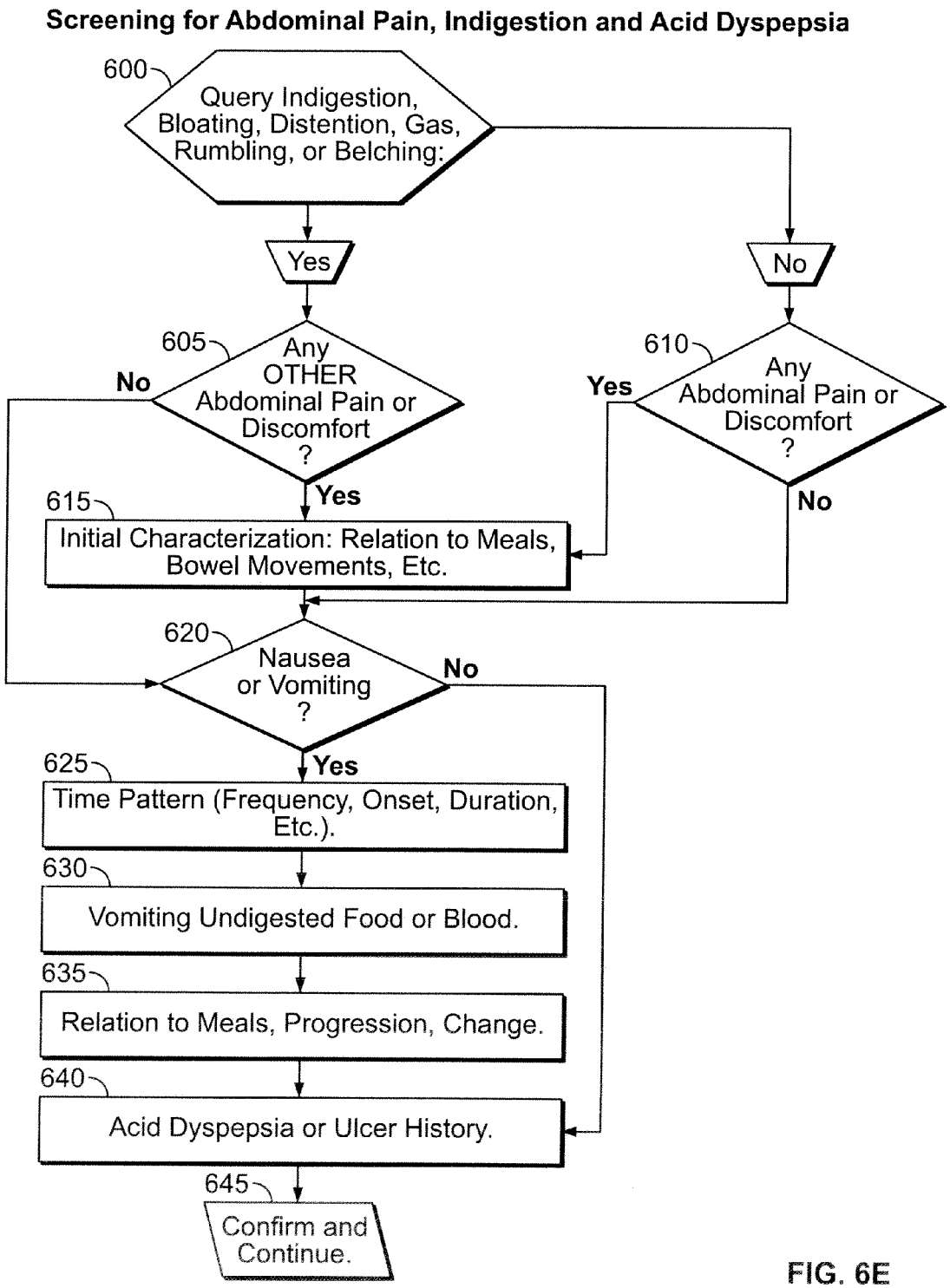
FIG. 6E is a flow chart of the program that screens for abdominal pain, indigestion & acid dyspepsia.

The next set of questions pursues common upper gastrointestinal symptoms and abdominal pain or discomfort in relation to defined syndromes (FIG. 6E). In block 600, the patient is first asked about indigestion (belching, upper bloating or fullness) during or after meals, gas, distention, and rumbling. If these symptoms are present, the patient is asked whether they have any other abdominal pain or discomfort, block 605. This simple step is essential because physicians often ask about discomfort without clarifying relation to these other common symptoms-despite the diagnostic value of this information. If the patient denies indigestion symptoms (block 600), they are asked whether they have any abdominal pain or discomfort, block 610. If present, additional screening questions about abdominal discomfort are posed: whether these symptoms occur during or after meals, in relation bowel movements, or are relieved with food, antacids, or other agents is also sought (block 615). A narrative summary of these symptoms is presented to the patient for confirmation, and the section is repeated if necessary. For positive symptoms such as bloating, distention, or gas, sufficient details are asked to characterize clinical significance. The patient is then asked about nausea and vomiting, and symptoms are appropriately characterized (block 620 to 635). At block 640, more detailed questions are asked about history of peptic ulcer or use of NSAIDs (non-steroidal anti-inflammatory drugs that cause gastrointestinal complications).

Figure 6F:
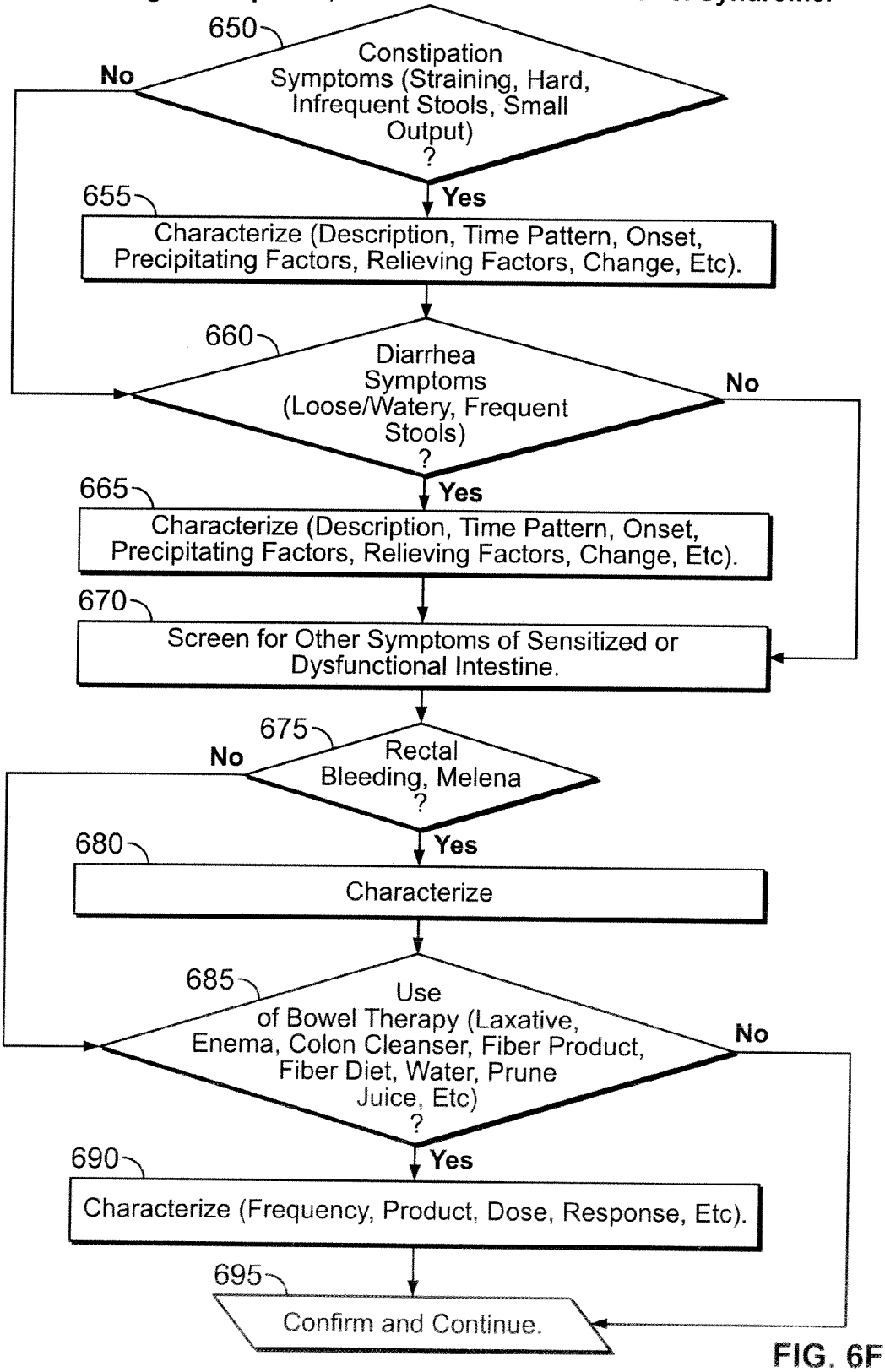
FIG. 6F is a flow chart of the program that assesses constipation, diarrhea and irritable bowel syndrome.

The last set of screening questions in this group is for bowel symptoms, FIG. 6F. Screening questions for constipation, block 650, and diarrhea, block 660, are presented. Because common medical terms are commonly misused or misunderstood by the public, CPM asks about specific features comprising a condition in simple terms, rather than using loaded medical jargon. Thus, the specific features that define constipation (hard stools, straining, or stools judged to be too infrequent by the patient) are assessed. However, additional measures of bowel problems are also queried, including stool frequency and consistency. Questions and criteria for identifying provisional problems accommodate the vagaries of these problems; for example, frequent passage of small amounts of hard stool is constipation, not diarrhea; and a single movement per day that is foul or loose may reflect an important "diarrheal" condition such as malabsorption. If screening symptoms for bowel problems are identified, then detailed characterization is sought (blocks 655 and 665). Screening for symptoms that may reflect a dysfunction, disease, or sensitized bowel are also sought, including incomplete evacuation, urgency, or bleeding (blocks 670 and 675). Use and benefit from various bowel therapies are also sought (blocks 685) and characterized (blocks 690); use of these agents may reflect specific bowel problems, preoccupation with bowel function, or abuse of agents that can cause long term morbidity (e.g., senna or cascara). Finally, the patient is presented with confirmation screens that permit repeat of indicated question sets (block 695).

Additional screening questions are summarized for several other areas in FIG. 6 (blocks 2100 to 2600), although these are not illustrated or described in detail. Additional questions complete a comprehensive "review of systems."

Initial identification of provisional problems. Identification of provisional problems is the first major step in implementing a problem-oriented approach to patient management, which is at the heart of this invention. Based on the information gathered in the screening section, provisional problems are identified. Complaints of abdominal or chest pain or discomfort are preliminarily categorized to facilitate further characterization, as outlined below:

1. Screening questions about known problems, such as heartburn, acid reflux, or angina.
2. Screening questions to elicit common symptoms such as bloating, distention, fullness, gas, or rumbling.
3. Screening questions about abdominal and/or chest pain and/or discomfort. If patients have these common symptoms, then they will be asked is they have any pain or discomfort in addition to these symptoms.
4. Identify the defining key features for symptom complexes (Table 3)
5. Based on this screening information, provisional problems or symptom complexes are identified (see Table 4 for a partial list). Identification of these problems is established by implementing simple Boolean logic to meet criteria established by an expert panel. Implementation of Boolean logic is in a flexible format that supports continual refinement.
6. Assign a provisional problem name linked to an ICD-9 code.

TABLE 4

Figure 7A:
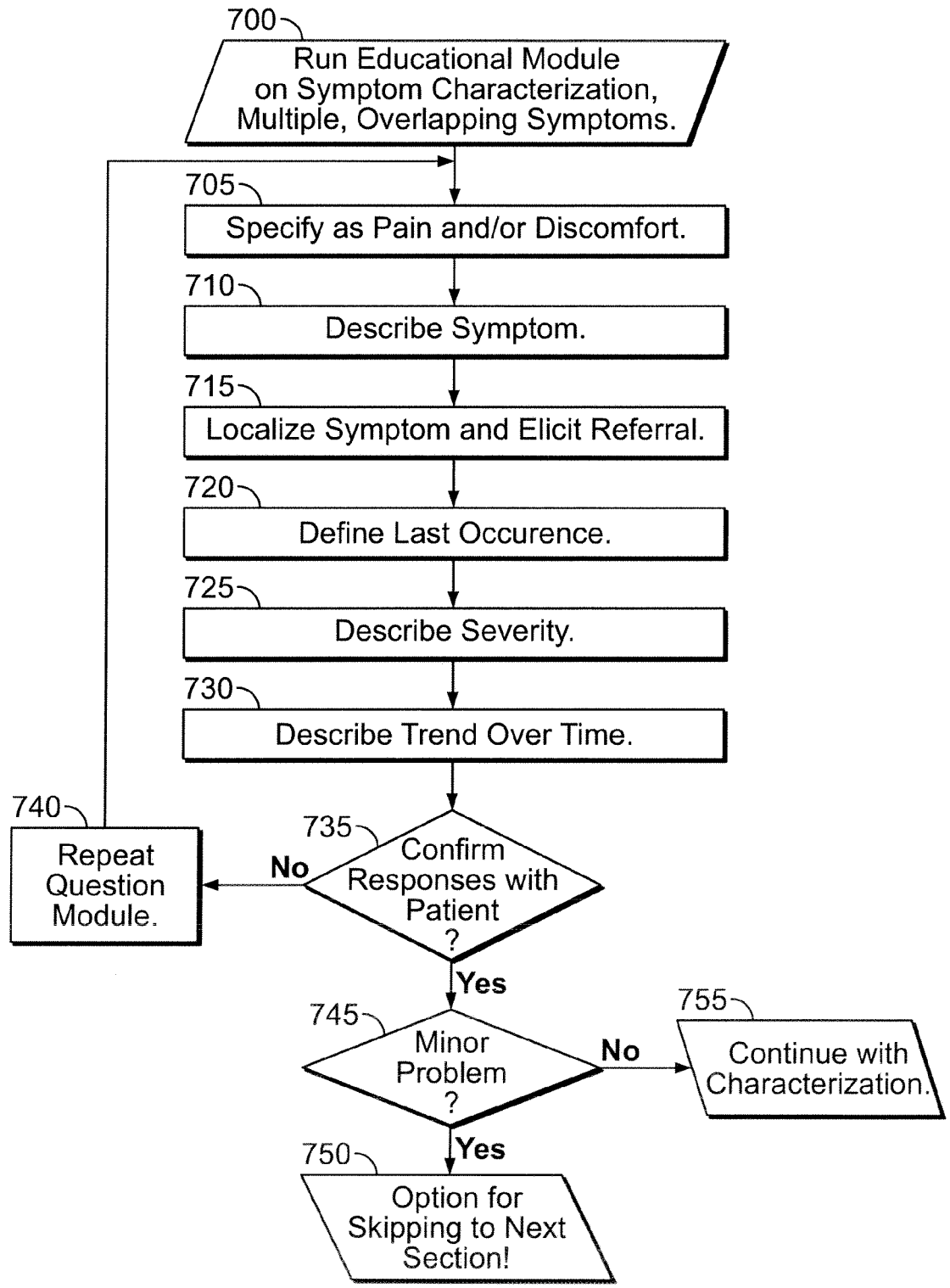
FIG. 7A is a flow chart of the program for general strategy for symptom characterization.

Partial List of Provisional Problems for Evaluation of Common Gastrointestinal, Pulmonary, and Cardiac Conditions Heartburn: burning discomfort under breastbone that usually radiated to throat
Acid regurgitation: regurgitation of burning or bitter fluid into throat
Angina or exercise-precipitated chest, neck, shoulder or arm discomfort or pain
Pulmonary pain: increased pain or discomfort with coughing or deep breathing or association of chest pain with coughing or shortness of breath.
Chest or abdominal wall pain: associated with local tenderness or increased with movement
Other chest pain or discomfort
Indigestion: upper abdominal discomfort occurring during or soon after meals usually associated with belching, bloating, or a sensation of stomach (upper abdominal) fullness
Acid dyspepsia: ulcer-like burning discomfort or pain occurring on an empty stomach and relieved with food, antacid, or antisecretory agents
Irritable (or sensitized) bowel: discomfort or pain associated with a change in bowel pattern or urge to defecate and/or relieved with decompressing the colon
Abdominal distention or bloating
Gas or rumbling
Other abdominal discomfort or pain
Diarrhea
Constipation
Anorexia: loss of appetite or weight loss
Nausea and/or vomiting
Dysphagia: difficulty swallowing
Odynophagia: pain with swallowing Characterization and discrimination of symptom complexes into provisional problems. This process is critical to complete the discrimination of provisional problems that will be presented as the CPM problem list for physician consideration. If the patient presents with only one pain or discomfort, it will be characterized as indicated in FIG. 7A, where the opening screens are a brief educational series on the characterization of pain using key features (Table 3) and on the likelihood of multiple, overlapping symptoms, block 700. As depicted by the screens in FIG. 5D, patients are then asked if they describe their symptom as a pain, a discomfort or both, block 705, as many patients are unwilling to call a symptom a pain when discomfort is the word that fits for them. To describe the pain or discomfort, patients are presented with several adjectives to select among, block 710. A body localization chart is displayed on block 715 in which they touch the areas where they experience the pain or discomfort; sequential touches change the color to indicate severity of the pain in that region. The body localization figure is divided into center, right, and left segments in the upper and lower chest, and upper, mid and lower abdomen. Other regions of the body are also segmented to indicate the location of pain. Alternatively, the patient will be given test options to describe the location of their symptoms. The patient is then asked when they most recently had the pain, to describe the severity, and trend over time (better, worse, same, or varying), blocks 720, 725, and 730. In addition to characterizing the problem, these questions identify minor problems (no recent occurrences, minor severity, and/or improvement or disappearance over time). The responses are confirmed with the patient, block 735. If criteria indicate that the problem is minor, the patient is offered the option (block 745) of skipping to the next section of characterization, block 750. If symptoms are not minor, the patient continues, block 755.

Figure 7B:
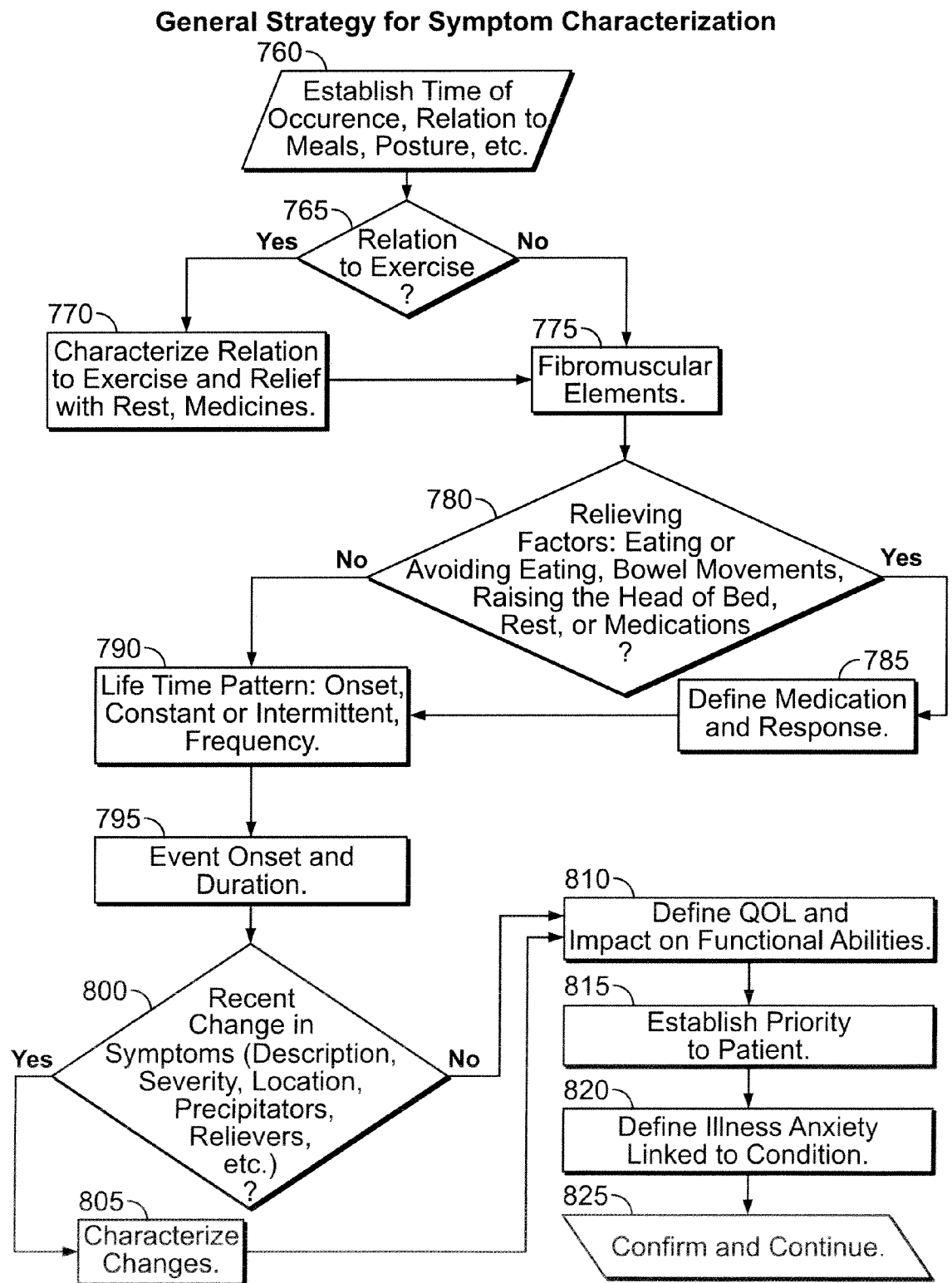
FIG. 7B is a flow chart of the program for general strategy for symptom characterization.

Additional characterization questions continue in FIG. 7B, where the times of occurrence and relation to activities, posture, sleep, meals, and exercise are established (blocks 760 to 765). If a relation to exercise is indicated, then the degree and consistency of occurrence and relief with rest and medication is sought because these data can implicate a cardiac etiology (block 770). Fibromuscular elements are sought in block 775, by asking such questions as whether there is local tenderness or precipitation by tightening the involved muscles, taking a deep breath, bending, or twisting. Cross referral and sensitization is common due to the convergence of the nerves to the viscera and body wall in the spinal cord and brain; visceral disease can frequently be associated with fibromuscular tenderness. Identifying a fibromuscular element is very helpful, often serving to clarify otherwise confusing pain and simplify the diagnostic process.

Relieving factors are asked about, since this information can provide important clues to diagnosis and appropriate therapy. Questions are asked about effects of rest, posture, eating or avoiding eating, and medications, block 780. Branching screens define specific medications, compliance and response, block 785. Additional questions are asked about the pattern over time, frequency, and onset and duration of episodes (Blocks 790 to 795). Finally in blocks 800 and 805 any changes in severity, description, location, and timing are sought and characterized because these changes can also provide important clues to the nature of the problem or to new problems. With the problem now defined, QOL measures are applied that determine the degree of impact on daily functions, such as walking, exercising, basic activities or household chores, working, socializing, or sleeping, block 810.

Figure 7C:
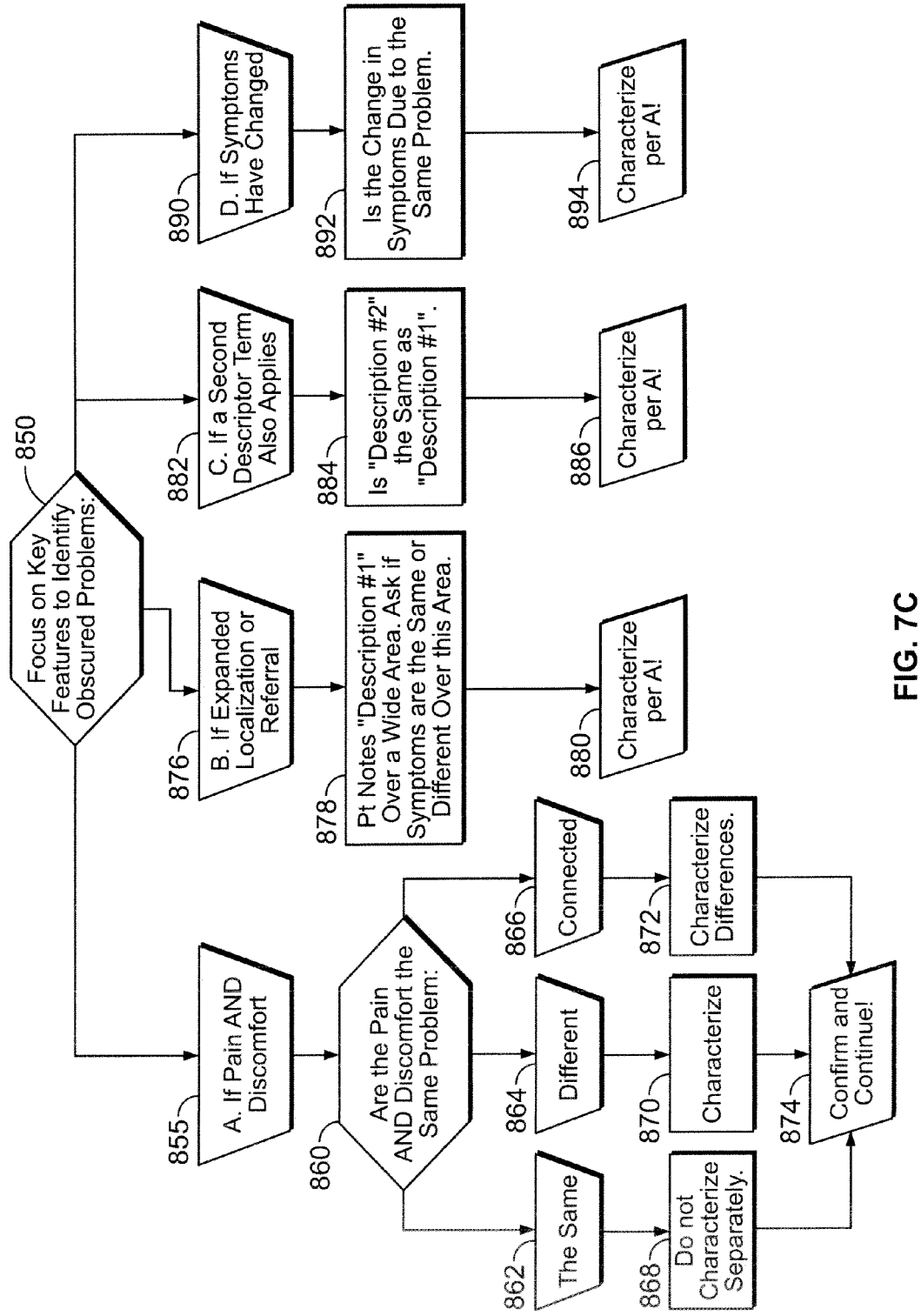
FIG. 7C is a flow chart of the program that helps in the detection of obscured symptom complexes.

Eliciting an obscure problem. It is common for patients to have a symptom complex that obscures a second problem. Identifying this second problem may facilitate the management process. The invention implements several mechanisms focusing in key features to identify obscured problems (block 850 in FIG. 7C). These steps are implemented at the conclusion of a characterization sequence, block 825 (FIG. 7B).

When patients are asked if symptoms represent a pain, a discomfort, or both, the choice of pain AND discomfort may indicate overlapping symptom complexes. For example, a pressing chest pain may be noted with exercise due to angina along with a dull, continuous discomfort due to a chest wall muscle ache. The patient might not know these are separate until they are teased apart. When patients report both pain AND discomfort (block 855), they will be asked if these represented problems that are the same, different or connected (Block 860). If symptoms are the same, no further characterization will be performed, block 868. If symptoms are different, block 864, detailed characterization (Blocks 705 to 820) will be presented. If symptoms are connected (related, but not the same), the differences will be characterized (block 872).

Localization may also provide a clue. Symptoms that are localized in broad areas or referred to other regions (e.g., chest pain that is also felt in the abdomen) may represent expanded referral of a single problem (a common phenomenon especially with functional gastrointestinal disorders) or two discrete disorders. When localization suggests expanded distribution block 875, the patient is asked to focus on the key features (how the pain feels and when it comes and goes) to decide if symptoms in these different regions represent the same or different problems, block 878.

When describing symptoms, the patient can select more than one adjective (e.g., burning, pressing, aching, etc.). If a second term is chosen, block882, the patient is then asked to consider whether the use of this second reflects the existence of a different or connected problem, block 884.

If a patient notes that her symptoms have changed, block 890, she is asked if the change in symptoms represents a change in pattern or key features, block 892. Is the changed symptom different, connected, or the same.

After patients complete characterizing the problems identified in the screening questions, they are asked if they have any other pain or discomfort. Instances of the importance of this type of distinction are offered in the examples section.

Figure 8:
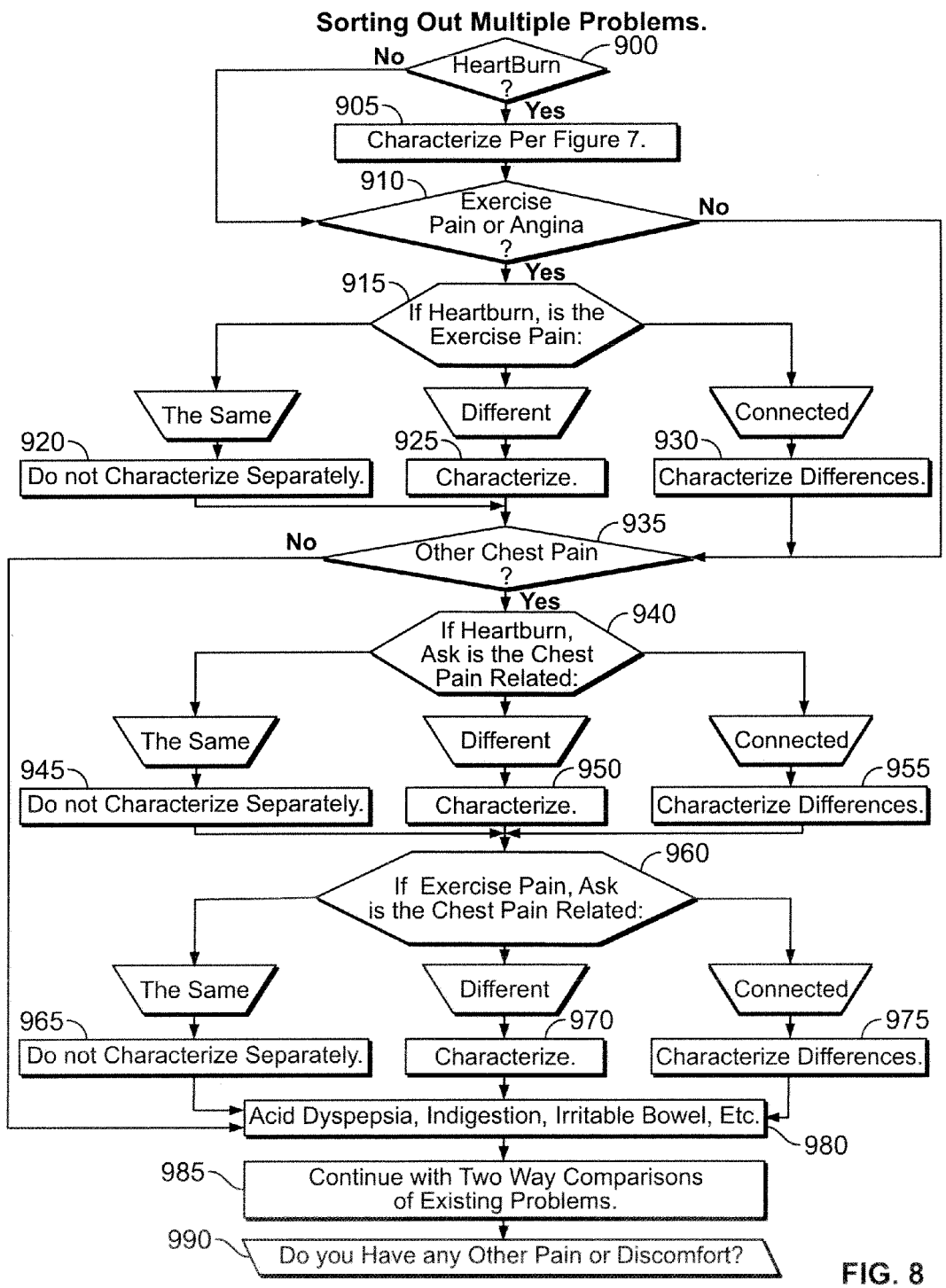
FIG. 8 is a flow chart of the program for sorting out multiple problems.

Discriminating multiple, overlapping provisional problems. Multiple, overlapping symptom complexes present a common challenge: they may be separate problems or they may in fact represent the same underlying process. These distinctions have a substantial impact on the diagnostic and therapeutic process. The invention is designed to improve the patient's ability to accurately describe multiple, overlapping symptom complexes and the physician's ability efficiently work with this information. If there appear to be multiple candidate provisional problems, several steps are involved in dealing with discriminating overlapping conditions. Each potential provisional problem (examples are listed in Table 4) is systematically characterized following the general format outlined in FIGS. 7A, 7B, and 7C:

1. Patients often cannot distinguish different symptoms until they have thought about the key features (Table 3). The strategy to dissect these problems is to ask the patient about the key features of each individual problem on its own and in relation to the other defined problems. This process is iterative until all problems and their interrelationships are defined. The logic of this process is depicted in FIG. 8. For example:
    If the patient screened positive for heartburn, block 900, then this symptom is characterized, block 905. If the patient screened negative for heartburn, screening variables for symptoms of exercise pain or angina are tested, block 910.
    If this test, block 915, reveals that both heartburn and exercise pain/angina are present, the patient is asked if these symptoms are the same, different, or connected.
        If the patient responds that these symptoms are the same, then the exercise pain is not further characterized, block 920.
        If the heartburn and exercise pain/angina are different, then the exercise pain is characterized in detail, block 925, using the strategy depicted in blocks 715 to 820.
        If the patient reports that these two symptoms are connected, then they will be asked which key features are different, block 930. In this case, only the features that differ will be characterized, branching through blocks 715 to 820.
    Logic continues at block 935, where the presence of another chest pain is tested.
        If no other chest pain is present, logic continues at block 960. However, if another chest pain is present, then the presence of heartburn is tested, block 940.
        If heartburn and another chest pain are present, the patient is asked whether the heartburn and this other chest pain are the same, different, or connected.
    Subsequent characterization, blocks 945, 950, and 955, depends on the answer (described above for blocks 920 to 935).
    Logic continues to test presence of exercise pain, block 960. If exercise pain/angina is present along with another chest pain, the patient is asked if exercise pain or angina is the same, different, or connected with this additional chest pain.

These two-way comparisons continue until all options have been examined. To facilitate the comparison, variable text functions are utilized so that the patient is asked about the specific problem they reported in the previous section. From a patient's perspective, this seemingly laborious process is rather simple when presented sequentially with specific, unimodal questions and questions relevant to their symptoms. Other strategies of discriminating overlap may also be developed, tested, and implemented by the inventive system.

1. An additional strategy to distinguish symptom complexes is to analyze typical patterns in real time. If a given symptom complex includes features that are not typical of a single disorder, such as a chest pain that is worse with belching (typical of acid reflux) but is also worse with exercise (typical of angina), the inventive system highlights this apparent contradiction for the physician's consideration during the patient evaluation.

2. The CPM analysis of symptom complexes may also reveal situations where symptoms apparently share features. Physicians will be informed of any apparent overlap. For example, if the patient has functional symptoms such as heartburn, indigestion, acid dyspepsia, and/or irritable bowel syndrome, this suggests the possibility of a widespread irritable gut. Although organic disease should be considered, this scenario is likely for functional disorders.

The value of attention to detail in history taking. The detailed history performed by the inventive system will improve clinical management.

1. Although many chest and abdominal symptoms are non-specific and overlapping, they can provide highly valuable clues to the underlying diagnosis and provide a starting point for effective management.

2. If multiple or overlapping symptom complexes are present, the failure to tease these apart or to recognize relations between them impedes the diagnostic process. Recognizing discrete problems (the separateness of two problems that the patient initially groups together) may reveal important underlying disease processes. Likewise, recognizing overlap (the association of two seeming unrelated symptoms) may simplify the diagnostic process.

3. The computer-aided, back-to-basics process provides the information necessary to detect changes in symptoms.

These changes may herald the emergence of a new problem that warrants clinical attention.

4. In addition, the information that is generated by this structured, consistent interview will build a knowledge base on a large number of patients. This database will allow the implications of symptoms to be recognized in a timely manner to optimize patient management.

5. Patients are educated and activated to know themselves, their symptoms, and how to communicate them. As patients are educated to provide their doctors with more accurate information about their symptoms, the history will prove even more useful in facilitating the diagnostic process. Although one might be concerned that this would exacerbate perceptions of pain, in reality, illness anxiety is usually alleviated by this educational process.

6. The inventive system provides the benefits of this detailed history for physicians who may lack the time and skills to extract this history themselves. In the process, physicians are trained to refine these skills that support patient-centered care.

Figure 9A:
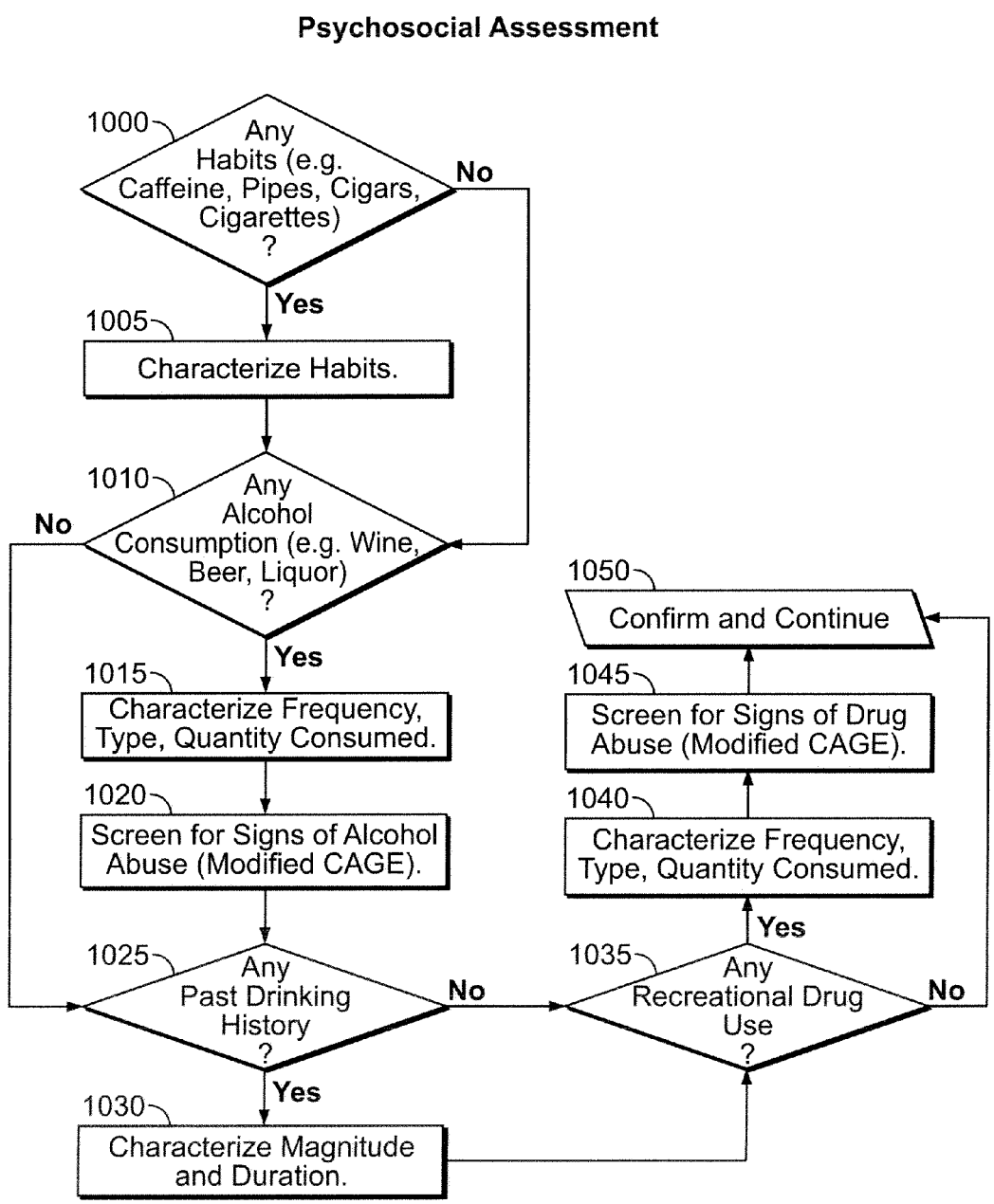
FIG. 9A is a flow chart of the program for psycho-social assessment.

Psychosocial screening assessment. Habits and substance use and abuse are screened for by the inventive system (FIG. 9A). For drug and alcohol consumption, questions are posed to allow patients to indicate alcohol consumption frequency from never to every day, block 1010. Quantities of wine, beer, and liquor consumed are then sought, using branching question sets to avoid posing irrelevant questions, block 1015. Questions are then asked to determine if alcohol use disrupts the patient's life, block 1020. Questions are also asked about past drinking history, block 1025, since prior heavy alcohol consumption has important health implications. A similar sequence of questions is asked for drug abuse, blocks 1035 to 1045.

Figure 9B:
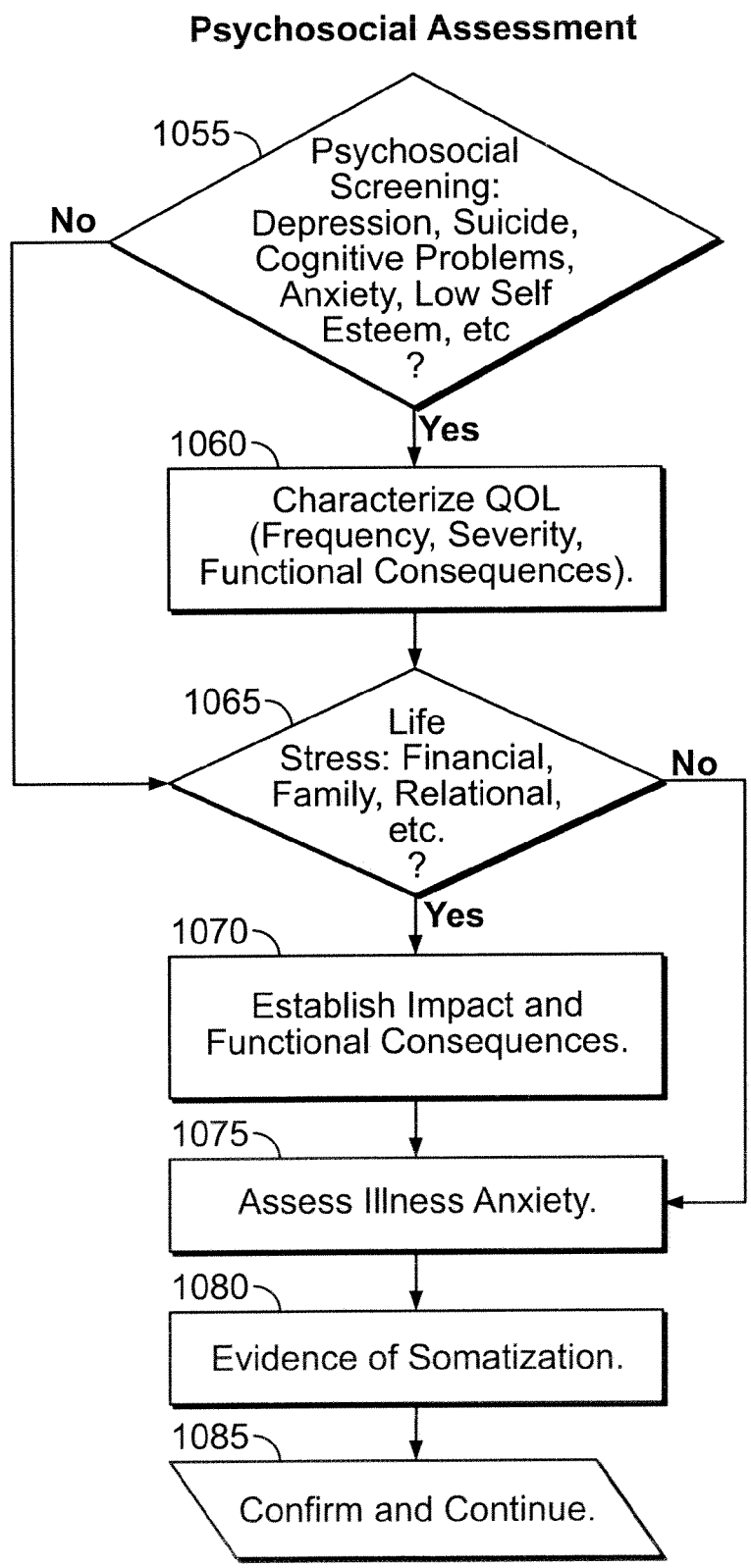
FIG. 9B is a flow chart of another program for psycho-social assessment.

Further psychosocial assessment is depicted in FIG. 9B. Screening for common psychologic comorbidity is conducted (e.g., domains of depression, anxiety, low self-esteem, etc.), block 1055. Questions are displayed on matrix screens that allow each response item to have up to 5 choice options, such as never, rarely, a little, some, and always (FIG. 9.1). These choice options can be scalar or categorical to measure how frequent and troublesome these domains are for the patient. It also allows patients to share more meaningful information about their symptoms without being pigeon-holed by limited binary responses, such as yes/no. Psychologic symptoms are grouped into domains, such as affective depression; suicide; cognitive dysfunction; anxiety; and low self esteem. Each domain comprises a scale with validity and reliability measures; the inventive system analyzes patient responses on the scale for each domain in real time and reports this information to the physician. When a patient scores moderate or high values on the scale for a particular domain, the degree of distress and functional impact is assessed, block 1060.

Life events that are perceived as stressful (e.g., trauma and illness, relationship problems, family problems, housing-related stress, financial pressures, legal problems, and work-related stress) are also assessed using scalar responses that indicate the degree of distress caused by the problem, block 1065. In addition, the impact and functional consequences of stressful situations are established, block 1070. Patient concerns about their illness, such as the presence of a serious underlying disease, the risks or ordeal of required testing or treatment, or poor future outcomes, are assessed in the sequence on illness anxiety related to specific conditions, block 820, or in general, block 1075. Recognizing and addressing these psychosocial issues has a significant impact on outcome of the therapeutic process. As described previously, the review of systems (FIG. 6) captures physical symptoms in several organ systems that may suggest somatization, a psychologic condition that can distract clinicians until recognized. At test block 1080, Boolean tests are performed to determine if sufficient criteria for somatization from the Diagnostic and Statistical Manual of Mental Diseases Fourth Edition (DSM-IV) are met. Symptoms that suggest somatization are recorded and presented to the physician in the CPM patient assessment report. Responses are summarized and presented to patients for confirmation, block 1085.

Figure 10:
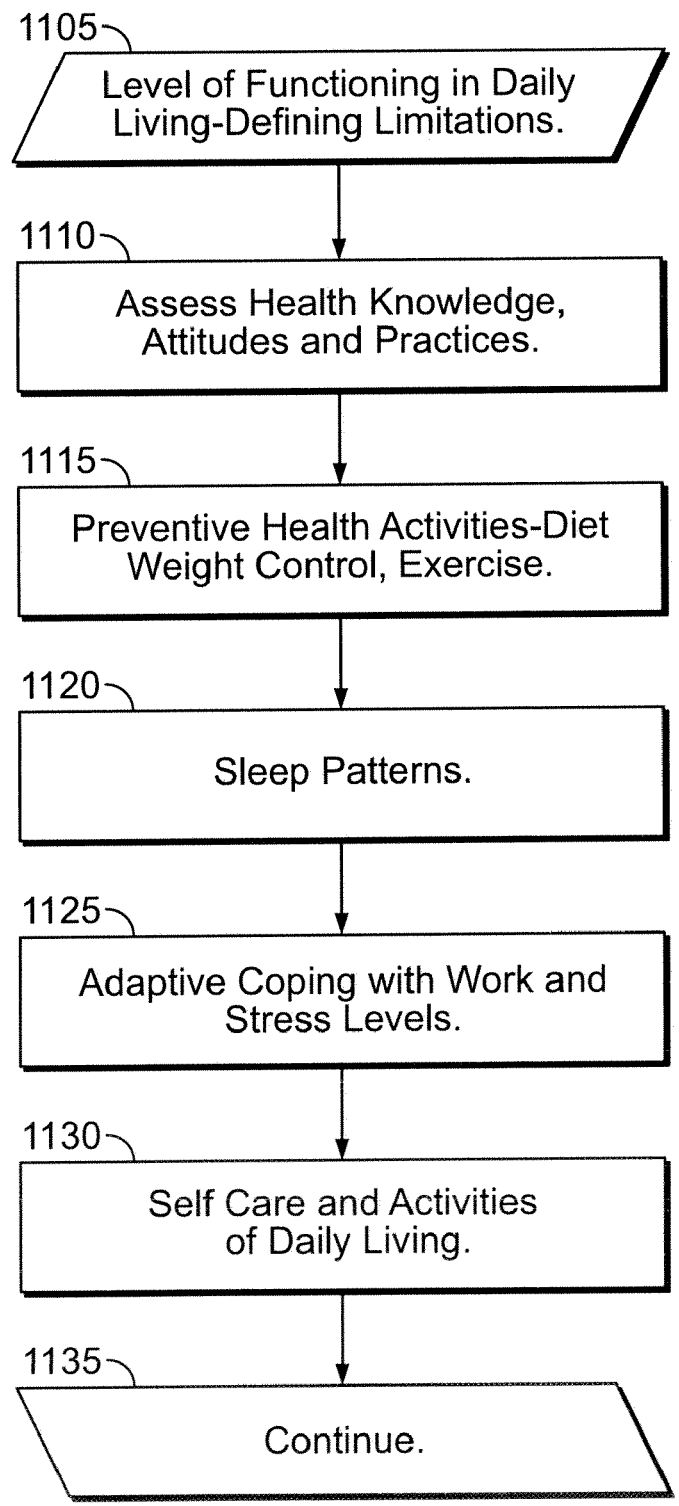
FIG. 10 is a flow chart of a program for general health status.

Logic continues in FIG. 10, to complete the medical history with questions about general health status (1100); level of functioning and activities of daily living (1105); health attitudes and expectations (1110); preventive health activities including diet, weight control, and exercise (1115); coping activities for stress (1115); and problems with self-care (1130). Additional information is collected on past medical history; medications and compliance behavior; allergies or untoward reactions to medications; surgeries, accidents, or injuries; other medical problems; and family history (not illustrated).

Formulating the agenda for the patient-physician encounter. As the interview proceeds, the invention formulates a provisional problem list based upon expanded criteria, adapted from those outlined in Table 4. As each subspecialty area is developed (Table 2), a set of Boolean criteria are created for each common symptom complex within the area. A mechanism has been established to test these criteria in three subsets (e.g., all of symptom set x, any of set y, and none of set z). As interview process proceeds, these criteria are tested. Problems are called "provisional" because the invention is not currently designed to make firm diagnoses, but rather to gather and process relevant, accurate patient data that allows the physician to designate problems or make diagnoses. The provisional problems that have been identified will be presented to the patient, asking whether review of these problems during this clinic visit is of high, medium, or low priority from their perspective. In addition, certain system criteria apply that automatically elevate some problems to high priority based on clinical importance, such as new onset chest discomfort, progressive difficulty swallowing, or blood in the stool. The problem list is presented to the physician in the order of priority. Associated symptoms and detailed characterization are summarized using a grammatical format with the variable text functions.

Patients are also asked if they have additional issues to address. Specific options are presented, such as problems with medications or concerns over future testing, treatment, or prognosis. Finally, patients are asked for any other questions, issues, or expectations from the visit. This patient input can be captured in a variety of formats, including recording wav files using the microphone system (block 90, FIG. 1) or keyboarding by the patient or clinic staff.

Figure 11A:
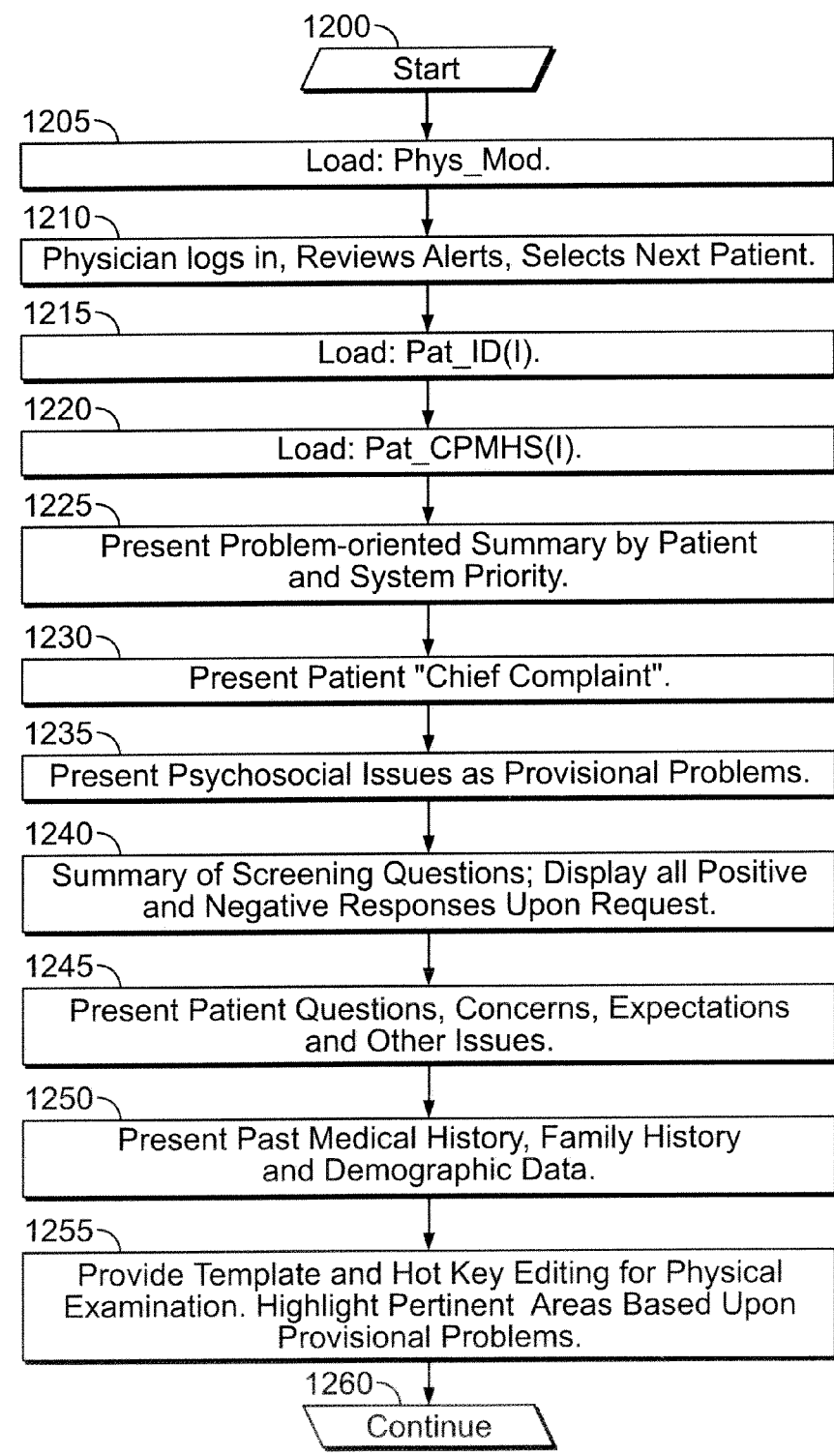
FIG. 11A is a flow chart of a program for patient assessment functions at the physician module.

Physician session. Before or at the outset of the patient interview, the physician accesses the CPM physician module to review the patient information as collected by the invention. Logic for the physician workstation is depicted in FIG. 11A. The process begins with loading the physician module, blocks 1200 to 1205. The physician then logs on, reviews notices regarding flagged problems, and selects the patient to be seen, block 1210. After selecting the patient, patient data, block 1215, and the problem-oriented health summary, block 1220, are loaded. The physician can then review each of the problems, including psychosocial issues and chief complaint, blocks 1225 to 1235. The physician can set filters to display all related information on each provisional problem, or display just the name and brief summary. The display includes summaries of screening questions; primary data can also be displayed at will, block 1240. In instances when the patient has been seen previously, additional information will be available for each problem, as indicated in Table 5. The workstation display also includes the patient's questions, concerns, and expectations, block 1245. Past medical, family, and social history are also displayed, block 1250.

TABLE 5

Problem-oriented Access to Patient Information
Data regarding specific problems are accessed with the following categories:

1. Problem name
2. Problem summary
3. Patient generated data by the inventive system:
   Initial: defining or clarifying related symptoms and key features
   Update: reassessment of symptoms, interval history, compliance with medication, lifestyle measures, etc.
4. Physician editing/comments regarding symptoms and history:
   Initial assessment
   Update
5. Physician-reported physical findings:
   Initial findings
   Updated findings
6. Relevant laboratory and procedure reports, pathology by date
7. Diagnostic and treatment plans, referrals, revisits, etc.
   Initial plans
   Updated plans
   Management milestones The dynamic, problem-oriented CPM record. From the physician's standpoint, dynamic, problem-oriented access to patient records is likely to be the most valuable element of the physician module. The ability to copy and update previous notes available on some electronic medical record (EMR) systems generates a large volume of redundant text, obviating some of the advantages that EMR offer for increasing data accessibility. With the proliferation of provider notes, it is often difficult to find information on management of any given problem. The invention makes data more accessible, allowing all information on a given problem to be readily found and retrieved. Information is organized and accessible by problem; the data for each problem are organized by date under the headings indicated in Table 5. A summary category is also available to capture an overview of the problem. The physician module allows filters to be applied to the data so that only the problem name and most recent entries are displayed. Alternatively, the physician can display data by other filters (e.g., all data, data by author, or another sub-category).

The name of the provisional problem is initially entered by CPM and updated by the physician. CPM data populates and updates the patient symptom history (item 3, Table 5). Laboratory data are populated by physician entry or query of provider EMR systems, and the physician selects management plans from a menu of management guidelines (items 6 and 7, respectively). Physicians have editing capabilities for all entries.

This strategy for dynamic, problem-oriented records provides quick access to primary information regarding a given problem. It reduces the risk of dilution of important information by unnecessary repetition. Physicians enter key information in summary blocks or by date. Economy of entries translates into greater accessibility of data. This dynamic problem list becomes the core of the medical record for capturing the patient-physician interaction.

Health prevention issues are processed as a "problem" entry for all patients. Interventions accepted in the provider organization are listed as sub-problems. These interventions might include vaccinations, or periodic screening tests such as pelvic examinations, Pap smears, or flexible sigmoidoscopy.

The physician can edit information gathered by the invention or add comments. In addition, if physician interview with the patient reveals incorrect data, the physician can reset the state of these variables. Boolean analysis of problems are then reassessed, based upon the new state of the variables. Physician editing is recorded separately so that the author of the changes and the source of the information are recorded. A template is also provided for the physical examination, with prompts for findings that may be important based upon the provisional problems. Hot key responses facilitate rapid reporting, block 1250 (FIG. 11A). Facility for computerized voice transcription can also be implemented when desired by the physician.

Figure 11B:
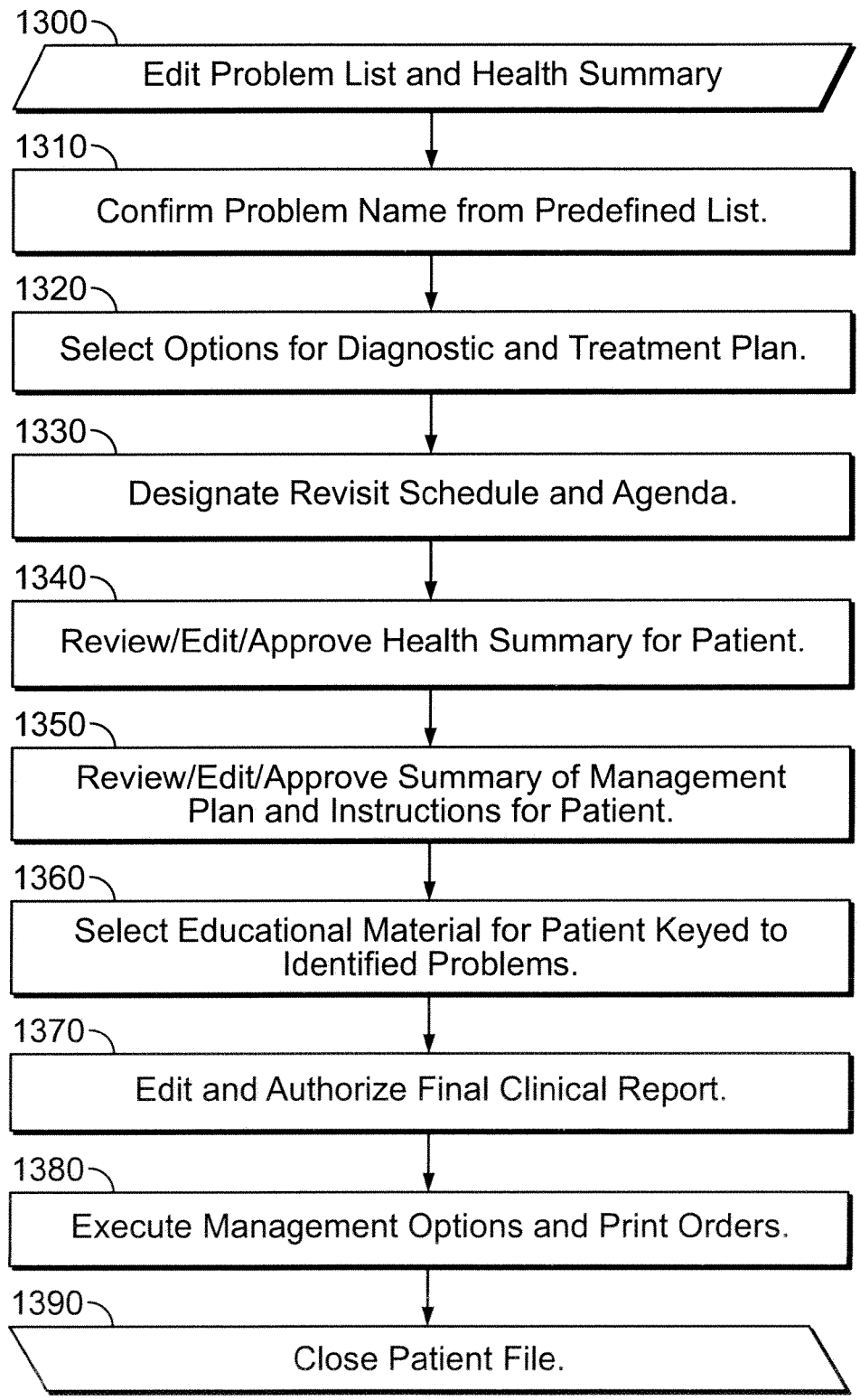
FIG. 11B is a flow chart of a program for physician management and reporting process.

After completion of the physical examination, the physician reviews and edits the problem list, block 1300 (FIG. 11B). Physicians can accept or modify problem names, block 1310, which are drawn from a predetermined list developed for each subspecialty by an expert panel. This index of standardized problem names is available for ready searching; hot keys are implemented so that the standardized problem name is displayed once a defining number of characters have been typed. Problem names are compatible with standardized nomenclature such as SNOMED, and linked to ICD-9 codes. This compatibility of CPM data assures ready communication with other information systems and useful for populating encounter forms and JCAHO-required problem lists.

Once problems are defined, management options linked to these problems (drawn from defined treatment guidelines) are displayed for selection, block 1320. Thus, the physician is given full control of decisions, but these decisions are facilitated by a menu of guideline options and then captured in the database. Management options include the following:

1. diagnostic tests (blood tests, procedures, radiography)
2. subspecialty referrals, for example, to gastroenterology, cardiology, gynecology, or surgery
3. other referrals, for example, for nutritional assessment, psychosocial/psychological, stress assessment and intervention, or somatic therapy
4. therapeutic options including indicated drugs (with dose, frequency, duration of therapy, side effects)

Data such as the indications, contraindications, preparation, risks, and benefits can be accessed for the selected diagnostic tests or treatment options. When a physician writes or accepts a drug from the menu, default settings for items such as standard dose are displayed for selection or editing.

The physician then selects the timing for revisits and the agenda of what will be done, block 1330. Follow-up scheduling could include plans such as the following:
  return for evaluation of response to therapy in "x" weeks
  discontinue medications at given time
  repeat endoscopy and biopsy in "y" weeks, or
  perform follow-up blood studies in 12 months.

Patients are given personalized instructions and education material when they leave the clinic. The physician selects this material for the patient from a menu of prepared text and graphics, block 1360:
  a health summary prepared for the patient based upon the identified problems and symptoms
  instructions for diagnostic studies, procedures, treatment plans
  instructions for self-care and lifestyle measures
  the agenda for future visits and consultations
  educational materials for identified problems The physician then reviews, edits and authorizes the final clinical report and execution of management orders (blocks 1370 and 1380).

Figure 12:
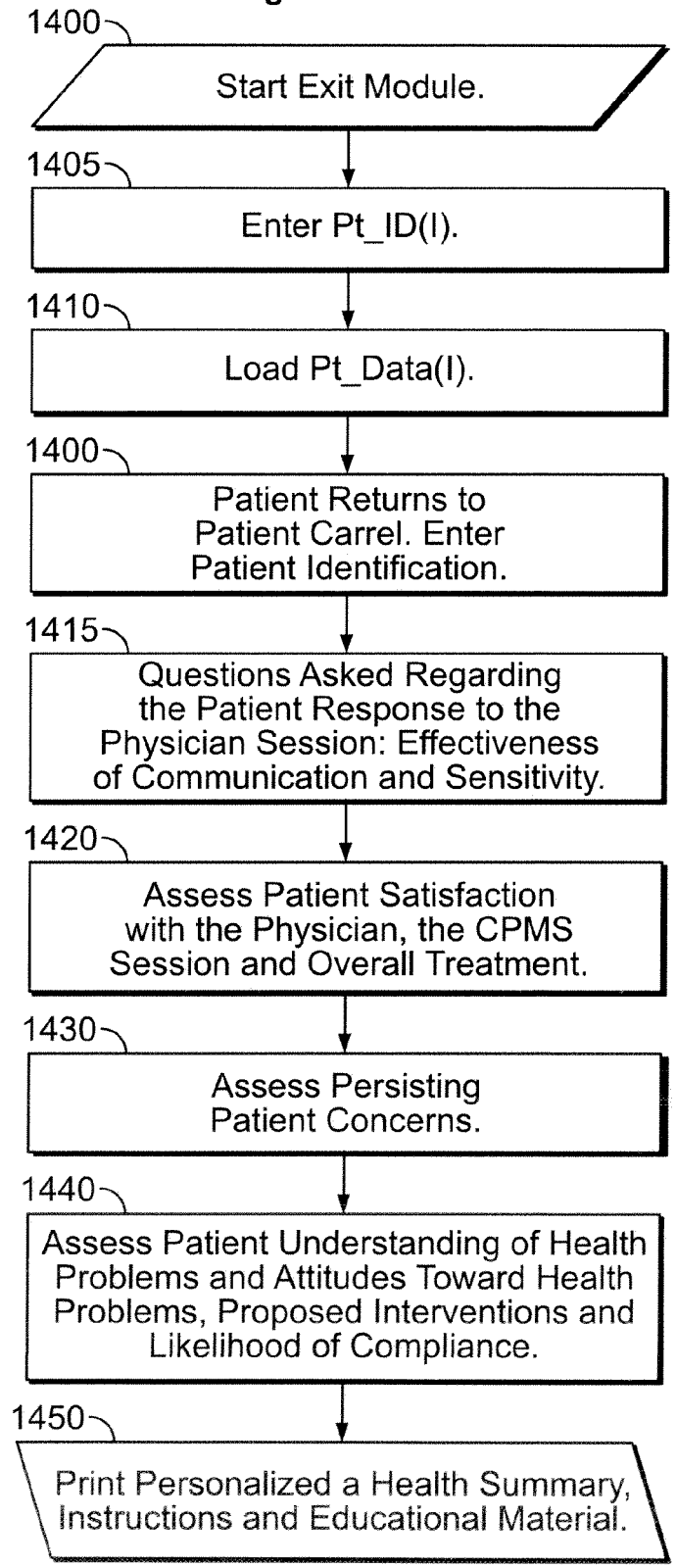
FIG. 12 is a flow chart of a program for functions and flow during exit session at the patient module.

Exit interview. After the physician visit, the patient returns to the CPM patient carrel for the exit interview. This sequence includes questions on the patient-physician encounter, attitudes towards compliance, illness anxiety, and any outstanding health-related questions or concerns (Table 6 and FIG. 12). Illness anxiety and health attitudes can be compared to the initial assessment to find the effect of the physician encounter on the patient's health concerns. A microphone or keyboard can be used by the patient or staff to enter the patient's persisting questions or health concerns. Finally, the patient is given a printed health summary, including their problem list, physician and follow-up instructions, personalized health education materials, and a reference on local resources, such as further instruction, counseling, support groups, websites, and hotlines.

The inventive system uses exit interview data to further support patient-centered care by providing individualized feedback to the physician on elements of the patient-physician interaction and patient health attitudes. These data are collected from the patient and fed to the physician on a per encounter basis. This information serves to educate physicians on the impact of their actions, effectiveness of their communication, and patient response over time.

TABLE 6

The Exit Interview

1. Assess the patient-physician encounter: interaction and communication. Questions include:
   Did the physician listen to the patient?
   Did the patient feel heard and understood by the physician?
   Did the patient understand the physician?
   Did the physician address the patient's concerns?
   Does the patient understand their condition and treatment as described by the physician (e.g., instructions for procedures, use of medications, other treatments, etc.)?
   Was the patient involved in negotiating a reasonable treatment plan (e.g., testing, prognosis, treatment, self-care, etc.)?
   Was the encounter rushed?
   Were the patient's expectations met?
2. Assess compliance attitudes. Questions include:
   Does the patient understand the treatment prescribed?
   Does the patient think the treatment is important?
   Does the patient think the treatment is reasonable?
   Does the patient foresee barriers to compliance? If yes, what are the barriers (e.g., financial, time-related, lack of social or technical support, lack of motivation, etc.)?
   Does the patient intend to comply?
   Does the patient want further instruction? (If yes, the patient has the option of running through an appropriate education module or clinic staff may be alerted)
3. Assess illness anxiety (adapted from psychosocial question sequence).
4. Capture open-ended patient feedback.
   Does the patient have any outstanding questions, concerns, or comments?

Completion of the exit interview concludes patient interaction with the inventive system until the patient's next visit. However, patients may access CPM in the interim from home (via the Internet or on a CPM CD-ROM or DVD) or at the provider organization for triage, screening, or health education sessions. Symptom updates are stored in the database. If CPM analysis of new patient information reveals a condition in need of prompt attention, the patient is instructed to seek care at the end of their CPM session. The patient's primary care physician is also notified of the patient's updated status via e-mail or an automated voice message or page generated by the inventive system. In any environment, early detection of problems improves the quality of care; in capitated environments in particular, this translates into lower overall health care costs.

Revisit strategy. The revisit sequence is called up when a patient who has previously interacted with the inventive system in a clinic setting (or online) returns to the clinic. The revisit module is loaded and started at block 1500 (FIG. 13), based on the results of test 315 (FIG. 5A). The data for the returning patient are loaded, block 1502, along with the revisit agenda generated by the physician at the conclusion of the previous session, block 1505. The patient is offered an orientation to the revisit process, block 1510. The patient's reason for the revisit is then sought (block 1515). Several response options are offered including items such as new symptoms (block 1520), change in status, concern or follow-up regarding a known problem (block 1540), or routine visit (block 1545).

The patient is also asked if she initiated the revisit or if the physician requested the revisit. The patient's perceived reason for the visit is compared to the physician's revisit agenda for follow-up care. This comparison provides a measure of care-seeking behavior. Understanding this behavior on a routine basis can be used to develop strategies to improve the overall cost-effectiveness of care.

If new symptoms are detected, the nature of these are sought and characterized (block 1525), branching to a specific module, as necessary, block 1530.

If the reason is follow-up or change in status of a known problem, or a routine follow-up evaluation, the patient's previous problem list with brief descriptions is presented, block 1550. The patient is asked if this problem list is accurate, block 1555. If incorrect, the patient can branch to characterization screens to correct errors, block 1560. When problems are confirmed, changes in status of each problem will be sought, block 1565. For example, the patient will be asked: "In the time since your last visit (the inventive system will substitute the exact period of time), is your burning, mid-chest discomfort better, worse or unchanged?" Change will be characterized, block 1570, seeking better insight into the nature of the symptoms or identifying new problems obscured by association to previous problems.

Patients are also asked about compliance with prescribed treatments and medications, block 1575, and satisfaction with that management. If the patient reports that she did not comply with any aspect of the treatment, reasons for noncompliance are sought. Changes may indicate cure, palliation, progression of an underlying disease process, or effects of other life events. If symptoms are better or gone, reasons for this positive change are sought, such as medication use or other treatment, just went away, changes in patient health behavior or life situation, or other factors, including psychosocial or stress elements. Returning patients are asked if they sought care from other health care providers for any reason during the interim period. If yes, reasons for seeking other care (e.g., physician referral to specialists or for procedures, desire for alternative care, etc.), types of care, and types of providers are recorded. Patient self-reports on compliance can be compared with other records of health care use for the interim period, such as laboratory and procedure reports, use of referral services, pharmacy records, and health care claims to comprise another measure of patient compliance with prescribed treatments. These data will be valuable in designing plans for individual patients or population subgroups, aggregated based on variables of interest such as demographic characteristics or health attitudes.

After pursuit of the primary reasons for the visit and determining status of known problems, the system loads the revisit screening sequence, block 1580, derived from the triage and screening strategy described previously (FIGS. 5 and 6). In this process the patient will go through an abbreviated review of systems and psychosocial screening to elicit new symptoms or changes developing during the interim period, block 1585. Any symptoms that are uncovered will be characterized, block 1587, in a similar fashion to that described previously.

The patient is asked for questions or other issues to be discussed with the physician, block 1590. Following completion of the revisit session with the inventive system, the CPM database is updated with new patient information and a problem-oriented report is prepared, block 1595. This report is immediately available for physician review at the physician workstation using a format designed for physician editing. After the physician revisit, patients return to the patient carrel to complete the exit interview.

Computer implementation of CPM process. Described herein is the design of computer system and its basic components that implement the functionality of the CPM system to facilitate and measure optimized clinical process. The computerized system that embodies the CPM concepts is a computation device that provides screen development-facility (CPM screen editor), script development facility (CPM script editor), and script interpretation-playback facility (CPM player). This modular design provides flexibility and scalability for computerized support of patient assessment, quality of life measurement, physician process, assessment of patient satisfaction and response to therapy, and capture of integrated, encounter-based process and outcome measures (i.e. linked to specific episodes of provider-patient encounter).

The CPM system does more than present question screens and collect data. What separates the CPM system from a simple question screen is the scope and integration of the multifaceted computer support of the CPM clinical process. The ability to support discrimination of several overlapping problems, branch through question sets, and create relevant output using highly sophisticated, but flexible Boolean logic systems and provide specific feedback to patients in grammatically-coherent format are essential features. The overall modular design supports another key feature of providing capacity to scale up the process to handle a wide range of medical disorders and facilitate editing and refinement of question screens and script files.

The CPM concepts for patient assessment could also be embodied in other systems: clipboards, paper, and other computational systems, but this would be laborious and would not provide the integrative functions achieve with the computer system. Programs written in a variety of languages and using a range of computer systems (IBM or Apple personal computers, minicomputers, mainframes, or other such distributed logical systems) could be used to support the CPM process.

The CPM system further comprises a physician-editor's tool-kit having four distinct "tools" used by the physician-editor to create clinical applications. Other tools of similar or equal scope will be apparent to the skilled artisan after having the benefit of this disclosure. The first tool is the script editor for supporting creation of scripts that control the flow of the presentation to the patient, screening for potentially important symptoms, data collection, provisional problem identification, and reporting to the patient and physician-user. The script editor uses an advanced point-and-click graphic user interface ("GUI") which shields the physician-editor from the complexities of the embedded presentation language, provides debugging facilities, eliminates syntactical errors and streamlines the learning curve. However, other interfaces could be utilized to accomplish the same goal.

The second tool is the screen editor and screen definition language. The screen editor is used by the physician-editor to design data collection screens and screens for presentation of information regarding use of the system or health issues, "reward" displays to encourage participation, feedback to the patient, and the like. Screens handle their own data capture operations, thereby removing considerable complexity from the controlling script. Screens can be reused at different points in a script with context-specific content. A point-and-click GUI handles all interaction with the embedded screen definition language.

A glossary editor is the third tool for supporting parallel scripts adapted for patient characteristics such as age, gender, educational level, and ethnic background. The glossary editor permits the physician-editor to design multiple content models of a given script. For example, initial screens can determine the patient's age and level of education and then select an appropriate glossary of content blocks. Targeting questions to subgroups is more effective than utilizing broad-spectrum questions for all patients. Patients will find the process more relevant, motivating them to use the system. This facility is integrated into the internal presentation and screen definition languages.

The fourth exemplary tool is the pattern set editor. Problem identification and provisional diagnoses are defined in terms of multiple, overlapping patterns of patient responses. The inventive CPM system employs an innovative pattern recognition engine that supports extremely flexible views of symptom data. The pattern set editor can be most easily implemented using a screen format with list boxes for each of the defining conditions (e.g., ALL of the criteria in one list, ANY of the criteria in a second list box, and NONE of the criteria in the third). This simple interface permits the physician-editor to define complex patterns within a large universe of possibilities. This simple presentation using a GUI interface with list boxes allows the physician-editor to refine the criteria for identifying symptom complexes or testing other criteria based upon experience with patients and physician-users. Other methods for efficiently and flexibly implementing Boolean logic are available through the script itself.

A preferred presentation engine (the player) runs in the corresponding patient carrel computer terminal and is summarized herein. Internally, a master interpreter controls the execution of clinical applications comprising scripts, screens, glossaries and pattern sets. Specifically, the interpreter performs the following functions:

1. displays screens (with internal multimedia elements);
2. analyzes patient responses to execute branching, context-sensitive scripts;
3. applies selected demographic-specific glossaries;
4. collects patient response data via script commands, screens, and inferences;
5. manages data variables and database updates;
6. uses pattern set targets within collected data to identify provisional problems;
7. utilizes instructions in the script to construct problem-oriented reports for patients and physician-users;
8. manages storage, display and printout of reports; and
9. provides a debugging environment for physician-editors during the development of clinical applications.

This basic software structure provides an extremely flexible, scalable approach to embodying the interviewing, diagnostic, and therapeutic expertise of the physician who designs his or her own protocol. This enhances clinical process by providing technology that utilizes a dynamic, problem-oriented structure to collect standardized patient assessment data and identify provisional problems. This same methodology links problems to management algorithms and facilitates information management.

EXAMPLES

Applying the System to Specific Patient Problems

The following examples are presented as illustrative modes of the invention but are by no means exclusive. One skilled in the art will no doubt be able to develop variations thereto and stay within the scope of the present invention after having the benefit of the disclosure herein. Although all patients are expected to go through the full system, only a few key steps are highlighted in the overview example for each patient.

Patient 1: Assessing Overlap and Health Concerns

This example demonstrates evaluation of a patient with overlapping gastroesophageal reflux disease (GERD) and abdominal pain, confounded by marked health concerns over a recommendation to have surgery for his acid reflux.

Initial triage and screening assessments. This patient is new to the system, so he went through the entire screening sequence.

Screening for chest and esophageal symptoms revealed a history of heartburn and a corresponding burning substernal pain, block 450. No other type of chest pain was noted (block 460-465).

The patient denied coughing or asthma (block 500); both symptoms can complicate acid reflux. He also noted no difficulty swallowing (block 550).

Screening for abdominal symptoms revealed abdominal discomfort that was present in a pattern that initially confused the patient. He responded to the screening questions that he did have an upper abdominal bloating discomfort and fullness immediately after meals. He also reported that abdominal discomfort that was associated with a change in bowel pattern and relieved with evacuating his colon (blocks 605 and 615). Additional screening questions documented diarrhea alternating with constipation and no blood in the stool (Blocks 650 and 660).

Detailed Characterization of Provisional Problems, Sorting Out Overlap, and Clarifying the Interrelations.

Detailed characterization of bowel function revealed diarrhea alternating with constipation that had been present for three decades. There was minimal change in the pattern and these specific symptoms were of modest severity from the patient perspectives (Blocks 655, 665, 670).

Detailed characterization of his chest discomfort was then performed (blocks 700-820). The discomfort was burning in nature and substernal in location. Systematic questioning clarified that symptoms were found only after meals, during the day, and not at night. There was no relation to exertion and there was a moderate response to drugs that inhibit acid secretion. System queries established that these symptoms has been worse recently (block 730) and only moderately responsive to therapy (block 780). Quality of life measures were then explored and linked to each of these problems, allowing the severity and frequency of symptoms to be determined (block 810). Disruption of the patient's ability to perform functional activities of daily living was then established. These quality of life measures allow quantitative assessment of the functional impact of these symptoms, which is used as a baseline to measure response to a given management strategy. The substernal localization, radiation to the neck and relief by anti-secretory agents led to a firm identification of acid reflux. This pattern was summarized for the patient for the purposes of confirmation (FIG. 14A). The CPM Boolean logic recognized this pattern of upright, daytime reflux based on daytime, post-meal, but not nighttime symptoms.

Since the patient has an acid-peptic disorder, detailed questions were asked about use of aspirin and other non-steroidal antiinflammatory drugs (both over-the-counter and prescription) (block 760). These questions are often ignored in busy practice settings.

Abdominal symptoms were then characterized in detail. The Boolean treatment of initial screening data identified two possible provisional problems (Table 4): indigestion and irritable bowel syndrome. Boolean criteria for indigestion as a provisional problem include upper abdominal discomfort that occurs during and immediately after meals, is associated with belching, bloating or fullness (sensation of overeating). To minimize patient confusion, the first step is to distinguish this "abdominal discomfort that occurs during meals" from the patients "burning, mid-chest pain" that was previously characterized (FIG. 14B). The patient indicated that his "abdominal discomfort that occurs during meals" was different from his "burning, mid-chest pain." This abdominal discomfort was then characterized using the strategy outlined in blocks 715-825. The patient had noted these symptoms had come and gone over several years. It was described as a bloating discomfort localized in the upper abdominal that came during or with 30 minutes after meals. Symptoms were worse after certain foods, fatty foods and onions in particular (block 760). This symptoms were summarized for the patients consideration and confirmation (FIG. 14C). These symptoms fit CPM criteria for "dyspepsia/indigestion."

The next step in logic was to address the "abdominal discomfort that was associated with a change in bowel pattern and relieved with evacuating his colon." Again, reference to this problem will be specific, so that the patient will have no doubt what is being references. Following the logic in FIG. 8, the next is to determine if this discomfort is different from the patient's "upper abdominal bloating discomfort that occurs during meals." FIG. 14D is presented to clarify this relation. The patient responded that he was not certain if these problems were different, so that detailed characterization using the strategy in blocks 715-820 was presented to clarify the situation. A summary of these symptoms is noted in FIG. 14E. These symptoms were long-standing and consistent CPM criteria established by an expert physician panel for irritable bowel syndrome and identification of this pattern prompted generation of a provisional problem: presumed "irritable bowel syndrome."

The patient was then asked if he had any additional chest or abdominal symptoms that were not covered and no additional complaints were reported.

Completion of the medical history and psychosocial assessment. Generation of problem list. Comprehensive screening for psychosocial comorbidity (block 1055), psychosocial stressors (block 1065), and illness anxiety (block 1075 and Table 7) revealed considerable patient concern about heartburn symptoms. The patient indicated concerns about the seriousness of his condition, the possibility of surgery, and potential consequences of the necessity for long-term treatment.

TABLE 7

Partial list of illness anxiety issues.
The inventive system assesses illness anxiety including patient concerns regarding:

severity and consequences of the disease
no available cure
uncertain diagnosis
physician did not understand the patient's concerns
physician did not understand the patient's symptoms
necessity of further tests and procedures
risks of tests and procedures
need to take medication long term
medication risks, side effects, and dependency
need for surgery
risks and consequences of surgery
changes in lifestyle and behavior needed to comply with treatment or promote good health
opportunity costs of treatment (e.g., time and financial costs)

General health status, health attitudes, and behaviors were then explored (blocks 1105-1130). This patient's psychosocial profile, general attitudes and health behaviors were positive, with no untoward health behaviors, such as smoking or drug abuse. Alcohol consumption was limited to occasional social use. However, the patient reported considerable trouble sleeping.

Issues presented to physician in the physician module. A summary of the patients provisional problems and other patient data were then presented to the physician for review at the outset of the patient evaluation session(blocks 1225-1250). The patient's chief complaints, questions and health concerns are also highlighted for consideration by the physician at the outset of the session.

Patient problems are presented in order of greatest concern to the patient, as determined when each problem was characterized (block 815). Clinically significant problems that are not prioritized by the patient are also presented. Characterization of symptoms, severity, frequency, and impact on quality of life are highlighted.

Relevant psychosocial domains are highlighted as provisional problems (block 1235). This is particularly important for illness concerns in this patient.

Review of symptoms, past medical history, and other patient data are presented for efficient review, so that the physician does not need to spend time collecting these data.

The physician has complete control of the problem list and can edit and restructure the list as necessary, thus reducing the time required to keep accurate and complete records.

A template is provided to facilitate the physical examination (block 1255). Key findings that should be sought are highlighted. For example, in this patient, a note would be added for the physician to note if tenderness is present reproducing either the chest or abdominal discomfort.

The physician then confirms the final problem list, block 1310. The confirmation entails selecting a final term with appropriate descriptors for each problem. ICD9 codes are assigned.

Treatment guidelines regarding diagnostic testing and management are then displayed for each final problem for physician selection, block 1320. The physician selects from available treatment options or enters their orders via keyboard or dictation.

The problem list. For patient 1, the problem list presented to the physician might be appear as follows:

1. Gastroesophageal Reflux: Upright Pattern, High Patient Priority
   a. Symptoms: burning substernal pain with radiation to neck and antisecretory relief.
   b. Time pattern: symptoms have been intermittent for 30 years, but of increasing severity recently.
   c. Complications: no evidence of local or respiratory complications.
   d. Prior workup: patient states prior radiography and endoscopy were performed and results were normal.
   e. Prior treatment: ranitidine: partial relief at 150 mg twice daily.
   f. Comment: patient is concerned about problems from long term antisecretory medication use and risk of surgery.

Management Recommendations: (For Physician Selection)
a. General instructions: instruct patient on lifestyle measures.
b. Medication:

COMMENT: Patient with partial response to therapy and high concern over problem. Consider a change in management.

Option 1:
Add medication: omeprazole 20 mg qd and
Discontinue ranitidine

Option 2:
Add medication: cisapride 10 mg qid.
Continue ranitidine 150 mg bid

Action Panel:
Current medication: ranitidine at 150 mg twice daily.
    Continue
    Discontinue
    Adjust dose New Medications:
Omeprazole 20 mg daily, 30 min before meals
Cisapride 10 mg qid, 30 min before meals and at bedtime 2. Dyspepsia: Indigestion Pattern, Probable.
   a. Symptoms: upper abdominal bloating discomfort that occurs during and after meals. Worse with fatty foods.
   b. Time pattern: longstanding, no change in pattern.
   c. Prior workup: patient states prior radiography and endoscopy were performed and results were normal. No known H. pylori testing or treatment.
   d. Prior treatment: ranitidine: no response Management Recommendations (Click Desired Measures):
   a. Reassurance: symptoms are longstanding, nonprogressive, and study were negative
   b. Stress/anxiety reduction
   c. Tricyclic antidepressants (amitriptyline 10 mg hs)
   d. Dietary modification
   e. Medication: cisapride trial: 10 mg qid before meals and hs
   f. Re-evaluation and repeat endoscopy if symptoms persist or worsen.

2. Irritable Bowel Syndrome, Probable
   a. Symptoms: crampy, gas-like mid-abdominal discomfort after meals. Relation to change in bowel pattern and relief with evacuation.
   b. Time pattern: longstanding, no change in pattern.
   c. Prior workup: patient reports negative barium X-ray study.
   d. Prior treatment: none.

Management Recommendations:
a. Flexible sigmoidoscopy
b. Fiber therapy (e.g., Metamucil 1-2 tsp po qd-bid)
c. Tricyclic antidepressants (amitriptyline 10 mg hs)

4. Illness Anxiety
a. Symptoms: concern over diagnosis and prognosis.

Management Recommendations:
a. counsel patient regarding excellent prognosis
b. reassess upon next visit
c. consider referral for additional psychological evaluation if patient concerns about health are inappropriate or if patient does not respond to treatment.

Advantages of the Inventive System for Patient 1:

Explanation and feedback is provided to the patient regarding symptoms. Symptom patterns are confirmed with the patient so that he becomes more fully aware of the symptoms and how to describe and communicate them to the physician.

The overlapping presentation is discriminated. CPM elicits and discriminates the three symptom patterns that are likely to be confusing if not recognized. This facilitates physician efficiency in collecting and interpreting the history.

The patient's enhanced understanding of his symptoms allowed the inventive system to generate a clear, detailed history for the physician.

A clear description of symptoms lessens anxiety of both clinicians and patients, reducing the need for extensive work-up and improving the therapeutic response.

Important psychosocial history pertaining to illness anxiety is elicited. This patient's concerns about what might be wrong with him and the potential consequences of the therapies that might be necessary caused him considerable concern. Focused questions regarding illness anxiety revealed these issues.

Overall efficiency of evaluation is improved, providing more time for important issues. Screening questions were pursued that eliminated numerous other potential problems, such as use of NSAIDs or aspirin in patients with acid peptic disease, thereby allowing the physician and patient to focus on the major problems.

Dynamic problem lists are incorporated into the clinical pathway. Assigning ICD-9 codes allows CPMS to generate a final problem list (required by Joint Commission on Accreditation of Health Care Organizations, JCAHO). More importantly, a dynamic problem list becomes an integral part of the evaluation and treatment process.

Accuracy and efficiency of reporting are facilitated. An encounter form necessary for billing and justification of time allocations is generated as a direct reflection of an accurate problem list. This output includes both diagnostic codes and treatment interventions. Time allocated to the encounter is recorded from the initial check-in of the patient to the physician signature on the final report.

What is claimed is:

1. A data processing system comprising:
   one or more computer processors programmed to receive health information from a patient using software operable to pose a logic-driven, branching series of questions to identify, discriminate current from past, and prioritize said patient's major symptoms,
   (a) wherein said major symptoms are ranked by priority to said patient; and wherein exploratory questions are used to survey selected topics;
   (b) wherein said exploratory questions ask about groups of related items;
   (c) wherein said exploratory questions determine a time frame of relevance to said patient and the priority of a symptom or provisional problem,
   (d) wherein said priority is characterized by one or more patient factors, selected from the group of: patient's priority for discussion with a clinician, severity of said symptom, impairment of functional abilities, impact on quality of life resulting from said symptom, or system criteria based on a potential clinical importance of said symptom;
   (e) wherein said software is further operable to construct subsequent, more detailed questions from a database of potential questions, based upon said patient's responses to said exploratory questions; and
   (f) wherein said software is operable on the one or more computer processors or on a server distributed to the one or more computers over an Internet connection.

2. The system of claim 1, wherein said system is operable to integrate an assessment of characterization detail for related symptoms in a group of potentially associated symptoms;
   (a) wherein potential associations between symptoms are identified at a time of authoring of interview content based upon clinical knowledge;
   (b) wherein severities of candidate symptoms in associations are obtained during the interview;
   (c) wherein a most severe symptom in an association (hereinafter "index complaint") is identified;
   (d) wherein characterization detail is obtained about one or more index complaints, as appropriate for clinical importance or relevance to said patient;
   (e) wherein an interview question is asked about whether any of said patient's other symptoms in said association share features in common with said index complaint;
   (f) wherein, where symptoms are associated or features are shared, no further characterization is performed, or subsequent interview questions characterizing associated symptoms are combined; and
   (g) wherein a risk of frustrating said patient is reduced by detecting relations between symptoms, when they exist, or allowing symptoms to stand alone, when no association is identified.

3. The system of claim 1 further operable to identify and measure severity and functional impact of a full range of multiple potentially overlapping physical and psychosocial symptoms in any combination;
   (a) wherein an assessment uses screening questions relating to physical and psychosocial symptoms;
   (b) wherein said psychosocial symptoms comprise at least one of the group of: substance use, depression, anxiety, stress, somatization, health attitude, behavior, illness concern, and anxiety;
   (c) wherein said overlapping physical and psychosocial symptoms comprise symptoms that are concurrent or that share location or other features potentially confusing to patients or physicians;
   (d) wherein related symptoms are grouped in order to facilitate assessment of symptom severity, frequency, impact on functional abilities, and quality of life; and
   (e) wherein separate scores are calculated for each of said symptom groups in order to determine whether said patient has one or more than one symptom complex and to separately assess severity and functional impact of each symptom group over time or in response to treatment for purposes of patient care, research, or quality assurance.

4. The system of claim 1 further operable to assess impairment in quality of life and functional abilities in relation to a plurality of symptoms and medical conditions;
   (a) wherein quality of life questions are created to probe limitations in a plurality of general domains that may be related to one or more underlying medical condition;
   (b) wherein said quality of life questions are asked without reference to whether a limitation is due to a health or emotional condition, symptoms, injury, or other problem; and
   (c) wherein impact of each group of related symptoms or each health condition is determined by asking about resulting severity, frequency, or perceived impact on quality of life.

5. The system of claim 4,
   (a) wherein said software is operable to display areas of general quality of life and functional abilities that said patient has reported are impaired, and to offer said patient choices about potential causes of such impairment; and
   (b) wherein said software is operable to sequentially display each of one or more general quality of life issues reported by said patient to be limited by symptoms or health conditions, list various symptoms and health conditions that said patient has reported are most severe, and offer response options to indicate a degree to which each symptom or health condition causes limitation of indicated general quality of life domains.

6. The system of claim 1 further operable to directly assess dimensions of the quality of care and provide feedback to clinicians or administrators about areas where action could be taken to correct apparent problems with said quality;
   (a) wherein said system is operable to display questions regarding one or more of: patient understanding of a health condition, patient health attitudes and behaviors, patient willingness to change health behaviors, patient perception of communication with a clinician and whether patients were heard and respected, patient observation about health care received, patient understanding of what to expect and what to watch out for regarding health conditions or treatment, patient understanding of treatment received, patient understanding of medications to be used, or patient compliance with medication and with treatment; and
   (b) wherein patient-reported quality of care data are integrated into a clinical report and flagged to identify problem areas; such quality improvement data are presented to clinicians with suggestions regarding correcting apparent problems with the quality of care; or said software provides brief and focused education to a patient who needs or desires additional information about said patienfs health condition.

7. The system of claim 1, further operable to calculate a severity score based on patient data regarding severity of symptoms;
   (a) wherein different levels of severity are assigned different values;
   (b) wherein symptoms from a similar region or system of a patient's body are grouped together, offering patients the option of confirming this association, after which a score assigned to each group is computed, and scores are reported to facilitate interpretation by a clinician with regard to relative importance of a symptom group and possible implications of observed symptom patterns, and given scores of a particular group across successive interviews of said patient, to reflect changes in severity over time; and
   (c) wherein scores are reported to facilitate interpretation by a clinician with regard to relative importance of a symptom group and possible implications of observed symptom patterns, and, given scores of a particular group across successive interviews of said patient, to reflect changes in status over time.

8. The system of claim 1, further operable to:
   (a) inform patients about routine procedures, surgeries or research for which informed consent is required, and using text, images, or video or audio presentations to educate the patient about said routine procedures, surgeries or research; and
   (b) obtain informed consent from a patient who agrees to undergo at least one of said routine procedures, surgeries, or research.

9. The system of claim 3 further operable to characterize key features and detect symptom patterns of potential diagnostic, or therapeutic, importance relating to characterization details, sensitization and cross-referral of nerves from viscera and body wall, and symptom reporting by the patient;
   (a) wherein detecting symptoms in exploratory questions optionally triggers a detailed, systematic characterization of features, including at least one of the group of: location, description, timing, precipitating factors, and relieving factors;
   (b) wherein multiple symptoms and the characterization details are gathered and interpreted, wherein the characterization details include at least one of the group of: expanded referral, overlapping patterns of precipitation and relief, use of multiple descriptive terms, and evidence of somatic (fibromuscular body wall) involvement;
   (c) wherein a history of prior symptoms, or an absence thereof, provides evidence of the patient's pattern of symptomatic response; and
   (d) wherein said symptom patterns and the characterization details provide information implicating altered sensitization and cross-referral of nerves from viscera and body wall, and psychobehavioral dimensions of symptom reporting by the patient.

10. The system of claim 3 further operable to discover, discriminate, and measure multiple symptoms and uncover symptoms obscured by overlap with other existing or new symptoms;
   (a) wherein targeted instructions are provided to educate the patient about a possibility of overlapping symptoms and how to discriminate the overlapping symptoms by focusing on characteristic features;
   (b) wherein multiple symptoms may be discriminated by the patient as the same or different, based upon questions about the characteristic features,
   (c) wherein obscured or overlapping symptoms can be suspected based upon a response indicating at least one of the group of: two symptoms overlapping in location, timing, characteristic features such as a pattern of precipitation or relief, a symptom being described as both a pain and a discomfort, having expanded referral (being felt over a wide area), a character of the symptom being described by multiple terms, or a symptom pattern changing over time;
   (d) wherein patients are offered an option of a response indicating that potentially overlapping symptoms are the same, related but not the same, different, or uncertain; and (e) wherein optional branching series of questions are provided to gather further details for: symptoms that are different or related but not the same, whereas subsequent questions are skipped for symptoms that are the same or where the patient is uncertain about a relationship of the symptoms.

11. The system of claim 1 further comprising a System Response Analyzer adapted to use logic to monitor the patient's responses for an inconsistent response, the inconsistent response triggering a detailed assessment of patient consistency and veracity.

12. The system of claim 1 further operable to generate an agenda for a clinic session, the agenda comprising a list of symptoms ranked by patient or system priority; wherein the agenda provides information for estimating a time required for a practitioner to see the patient and a skill level of the practitioner required to see the patient.

13. The system of claim 1 further operable to support problem management by physicians, wherein symptoms and active medical conditions (such as diabetes, chronic lung disease), are presented as a problem;
(a) wherein a physician module is provided to filter, sort, and review patient-entered, physician-entered, or system-imported data, and to add physician-entered data;
(b) wherein the problem name is editable by the physician;
(c) wherein the problem can be created, updated, merged or divided by the physician;
(d) wherein all data can be linked to a provisional problem, automatically by the physician module, or by the physician;
(e) wherein data entered by the patient or the physician, or imported by the system can be linked at entry or by system criteria; to at least one type of data selected from the group of data for: initial and return visit, symptom, medical condition, medical history, physical finding, test result, treatment type, response to treatment, side effects from treatment, plan for diagnosis, treatment plan, or problem summary; and
(f) wherein data can be filtered, sorted, and presented by criteria, the criteria providing a problem, data, physician author, activity status(active or inactive problem), or data type.

14. The system of claim 1 further operable to support a return visit by the patient;
(a) wherein an agenda for the return visit may be set by: a return visit agenda set by a physician at a prior visit, completion of remaining interview modules from the prior visit, research protocol, or administrative protocol, wherein the administrative protocol gathers quality assurance data;
(b) wherein at the return visit, the patient is queried about any reasons they have for the return visit;
(c) wherein the patient's reason for the return visit can be compared with a physician's reason for the patient's return visit;
(d) wherein the patient is provided an option to review and update their prior symptoms and responses;
(e) wherein other symptoms are optionally surveyed to ascertain new developments; and
(f) wherein use of prescribed treatments by the patient can be sought as a measure of compliance.

\* \* \* \* \*

UNITED STATES PATENT AND TRADEMARK OFFICE
CERTIFICATE OF CORRECTION

| | | |
|---|---|---|
| PATENT NO. | : 7,593,952 B2 | Page 1 of 1 |
| APPLICATION NO. | : 09/289044 | |
| DATED | : September 22, 2009 | |
| INVENTOR(S) | : Soll et al. | |

It is certified that error appears in the above-identified patent and that said Letters Patent is hereby corrected as shown below:

Please amend the specification by adding the following heading and paragraph immediately above the "Field of the Invention" heading on page 1:

Government License Rights
This invention was made with government support under grants DK53726 and DK55488 awarded by the National Institute of Diabetes and Digestive and Kidney Diseases at the National Institutes of Health. The government has certain rights in the invention.

Signed and Sealed this
Sixth Day of November, 2012

David J. Kappos
*Director of the United States Patent and Trademark Office*